US007273964B1

(12) United States Patent
Cattaneo et al.

(10) Patent No.: US 7,273,964 B1
(45) Date of Patent: Sep. 25, 2007

(54) NON-HUMAN TRANSGENIC ANIMALS FOR THE STUDY OF NEURODEGENERATIVE SYNDROMES

(75) Inventors: Antonino Cattaneo, Trieste (IT); Simona Capsoni, Trieste (IT); Francesca Ruberti, Trieste (IT)

(73) Assignee: Scuola Internazionale Superiore Di Studi Avanzati, Trieste (IT)

( * ) Notice: Subject to any disclaimer, the term of this patent is extended or adjusted under 35 U.S.C. 154(b) by 227 days.

(21) Appl. No.: 10/049,306

(22) PCT Filed: Jul. 28, 2000

(86) PCT No.: PCT/IT00/00321

§ 371 (c)(1),
(2), (4) Date: Jun. 5, 2002

(87) PCT Pub. No.: WO01/10203

PCT Pub. Date: Feb. 15, 2001

(30) Foreign Application Priority Data

Aug. 6, 1999 (IT) .............................. MI99A1783
Jun. 5, 2000 (IT) ........................ RM2000A0306

(51) Int. Cl.
*A01K 67/027* (2006.01)
*A01K 67/00* (2006.01)
*C07H 21/04* (2006.01)

(52) U.S. Cl. .......................... 800/18; 800/9; 536/23.53
(58) Field of Classification Search .................... 800/8, 800/9, 12, 14, 18; 530/387.1
See application file for complete search history.

(56) References Cited

FOREIGN PATENT DOCUMENTS

EP 0921189 6/1999
WO WO 92/08483 5/1992
WO WO92/08483 5/1992

OTHER PUBLICATIONS

Catteneo et al (Society for Neuroscience Abstract 301.18, 1996).*
Kappel et al (Curr. Opin. Biol. 3: 548-553, 1992).*
Melton (BioEssays 16(9): 633-638, Sep. 1994).*
Moreadith (J Mol. Med. 75:208-216, Mar. 1997).*
Mullins et al (J. Clin. Invest. (1996) 98(11), Supplement S37-S40).*
Ebert et al (Mol. Endocrinol. 2(3) : 277-283, 1988).*
Hammer et al (J. Anim. Sci. 63 : 269-278, 1986).*
Wall (Theriogenology 45: 57-68, 1996).*

(Continued)

*Primary Examiner*—Richard Schnizer
(74) *Attorney, Agent, or Firm*—Law Office of Kenneth K. Sharples

(57) ABSTRACT

A non-human transgenic animal that is transgenic for an antibody or fragments thereof and having a phenotype reminiscent of human pathology. The human pathology includes neurodegenerative syndromes, muscular atrophy/dystrophy and immune disorders. The animals may be used in a method for early diagnosis of neurodegenerative diseases. The method includes monitoring the occurrence of the tau hyperphosphorylation and/or amyloid deposition in the back or lower limb skeletal muscle sample of a subject. Cells are derivable from the non-human transgenic animal and secreting the transgenic antibody. The cells are used for the selection of molecules pharmacologically effective in neurodegenerative and/or muscular pathologies and/or immune disorders. A non-human transgenic animal may be prepared by providing a first non-human transgenic parent animal for the light chain of an antibody and a second non-human transgenic parent animal for the heavy chain of the same antibody, breeding the two transgenic parent animals and selecting the progeny expressing both the light and the heavy chain.

12 Claims, 38 Drawing Sheets

OTHER PUBLICATIONS

Ruberti et al (J. Neurosci 20(7): 2589-2601, Apr. 2000).*
Capsoni et al (J. Neuroscience Res. 59:553-560, Feb. 2000).*
Piccioli et al (Neuron 15: 373-384, 1995).*
Cattaneo et al (Society for Neuroscience Abstracts 22 (1-3): 753, 1996).*
Hogan et al (In Manipulating the Mouse Embryo, Cold Spring Harbor Laboratory, Cold Spring Harbor, NY, p. 81, 1986).*
Capsoni et al (Proc. Nat. Acad. Sci. USA 97(12): 626-6830, 2000).*
Ruberti et al (Cell. Mol. Endocrinol. 13(5): 559-568, 1993).*
Cattaneo et al (J. Neurochem. 50(4): 1003-1010, 1988).*
Molnar et al (Eur. J. Neurosci. 10: 3127-3140, 1998).*
Nanduri et al (J. Neurosci. Res. 37(4): 433-444, 1994).*
Connor et al (J. Neurosci. Meth. 65: 93-99, 1996).*
Werth et al (Exp. Neurol. 161:203-211, 2000).*
Poul et al (Immunotechnology 1: 189-196, 1995).*
Piccioli P et al, Neuron 1995, 15(2):373-84.
Cattaneo A et al., Society for Neurosci. Abstracts, vol. 22, No. 1-3, 16, Nov. 1996, p. 753.
Chen Karen S et al., J of Neuroscience, vol. 17(19), 1997, pp. 7288-7296.
Capsoni et al., PNAS, vol. 97(12), 2000, pp. 6826-6831.
Ruberti et al., J. of Neuroscience, vol. 20(7), 2000, pp. 2589-2601.
Capsoni et al., J. Neurosci. Res 2000, 59(4): 553-60.
XP000102376.
XP001023821.
XP002177092.
XP001023701.
XP000102377.
XP001023836.

* cited by examiner

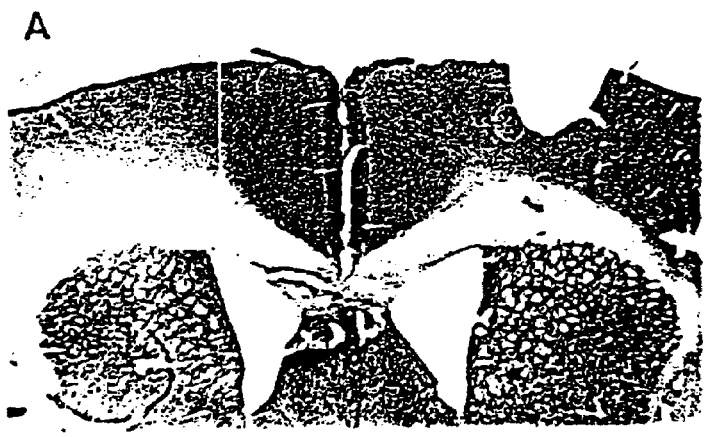
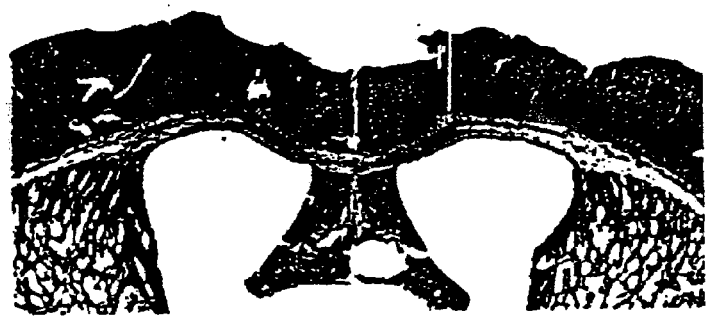
FIG. 5

CONTROL : 1.282 +/- 0.059

FAMILY #1: 0.879 +/- 0.033

A
B
FIG. 6

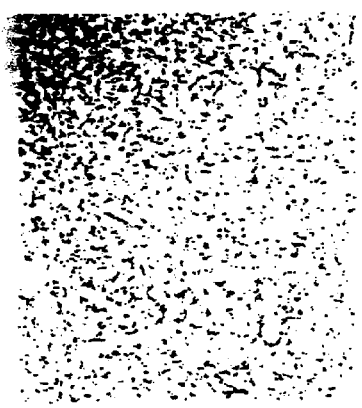
FIG. 8

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: R156 primer oligonucleotide

<400> SEQUENCE: 1
aaccatatat tcggtcgctg aggc                                              24

<210> SEQ ID NO 2
<211> LENGTH: 7
<212> TYPE: PRT
<213> ORGANISM: Artificial Sequence
<220> FEATURE:
<223> OTHER INFORMATION: phage peptide 18

<400> SEQUENCE: 2

Arg Gly Ser Arg His Asp Leu
1               5

NON-HUMAN TRANSGENIC ANIMALS FOR THE STUDY OF NEURODEGENERATIVE SYNDROMES

TECHNICAL FIELD

The present invention relates to non-human transgenic animals as model study for human pathologies, being transgenic for an antibody. More in particular the invention relates to non-human transgenic animals for anti-NGF (Nerve Growth Factor) antibody able to mimic different pathologies, as neurodegenerative syndromes, to be used as a model to study said pathologies and provide therapies therefor.

BACKGROUND

The Nerve Growth Factor (NGF) (Levi-Montalcini, 1952) is a pleiotropic neurotrophin having a fundamental role in the neuronal differentiation of central and peripheral nervous system. Accordingly NGF is essential for the differentiation of cholinergic neurons of the basal forebrain, the sensory and sympathetic neurons.

NGF is also necessary in post-differentiation steps, as it is able to modulate cellular apoptosis (Davies, 1992), the synthesis of cytoskeletal elements during neuroaxonal regeneration (Snider, 1989), the synthesis of enzymes, peptides and neurotransmitters (Eide et al., 1993), synaptic rearrangements and neuronal proliferation (Schnell et al., 1994). NGF is thought to play a fundamental role also in neurodegenerative processes and neuronal ageing (Connor & Dragunow, 1998).

The mechanisms regulating such different activities are yet to be clarified: the pleiotropic activity of NGF and the unavailability of adult animal models in which NGF activity is neutralized do not allow to relate its expression to a unique and definite phenotype or prefixed and recognisable function. The inactivation of NGF in adult animal models has been attempted by different approaches, among which immunoneutralisation by systemic delivery of anti-NGF neutralising antibodies (Levi-Montalcini et al., 1960) o gene <<knockout>> in transgenic mice (Crowley et al., 1994).

However in both cases the results were rather disappointing. The systemically delivered antibodies do not cross the blood-brain barrier and the effect of NGF neutralization in the other districts depend on many additional factors which are not easily standardised, like anti-serum titer and affinity, clearance rate or cross-reactivity of polyclonal antibodies with other neurotrophins, etc.

On the other hand the <<knockout>> approach in mice allowed to confirm the importance of said neurotrophin during development and the lack of redundancy of its own intracellular signalling system, but it failed to provide the expected adult model for the study of the NGF: indeed $ngf^{-/-}$ transgenic mice die shortly after birth, before the development of phenotypic changes linked to ageing. The phenotype of $ngf^{+/-}$ heterozygotic mice was also not very instructive, to study the phenotype associated with NGF deficit in adult: the NGF level in the heterozygous mouse is only 25% lower than in the control. This yields only a mild phenotype characterized by a faint cholinergic deficit, without apparent anomalies related to human neurodegenerative pathologies.

However different lines of experimental data suggest that NGF plays a key role in neurodegenerative syndromes (Connor & Dragunow, 1988). Senile dementia and Alzheimer's disease (AD) are neurodegenerative syndromes characterised by a progressive dementia. Alzheimer's disease affects 5% of 70 years old people and more than 30% of 80 years old people. Its incidence, in relation to the improvement of the life conditions and lengthening of the mean age, is destined to double in the next thirty years. Social costs for said pathology are very high. Alzheimer's disease mainly affects neurons of the cerebral cortex and the hippocampus and is characterised both by clinical symptoms (for example, the progressive loss of cognitive capacities) and by characteristic histopathological hallmarks (which can be diagnosed only post-mortem), as the formation of extracellular plaques of β-amyloid protein, neurofibrillar intracellular aggregates (tangles) consisting of hyperphosphorylated tau protein, and <<neuronal loss>> (Goedert, 1993; Mandelkow and Mandelkow, 1993; Selkoe, 1994). In the central nervous system basal forebrain cholinergic neurons are particularly affected, resulting in a decrease of acetylcholine synthesis and selective loss of said neurons. Cholinergic neurons are dependent on NGF, which acts through high (TrkA) and low affinity (p75) receptors.

Furthermore, Alzheimer's disease is associated to motorial disorders due to loss of cognitive capacities and coordination, as well as to pathologies of skeletal muscles such as amyloid deposition in skeletal muscle cells (Fukuchi et al., 1998; Jin et al., 1998). It is interesting to point out that NGF further exerts a function on non-neuronal cells, due to the presence of NGF receptors, namely p75 and TrkA, on non neuronal cells, including muscle cells.

In spite of enormous investments, up to now an early diagnosis and a suitable therapy for AD are unavailable. This is due, above all, to the unavailability of experimental cellular or animal models that mimic in a complete and accurate way the formation of the aberrant neuropathological structures found in AD brains. During recent years different transgenic models have been produced, with the aim of defining the aetiopathogenesis of Alzheimer's disease and of selecting useful compounds for therapy. Based on the histological, immunological, and molecular hallmarks of Alzheimer's disease, such as the presence of deposits of β-amyloid protein in the central nervous system, transgenic animals were obtained wherein the wild-type β-amyloid precursor protein (βAPP) is expressed at levels higher than the endogenous one, or is expressed in a mutated form wherein the mutations are those found in the genetic forms of the disease (Hsiao, WO 97/87492 and Games, WO 96/40896). Other transgenic models relate to animals wherein the transgene is the presenilin-1 or -2 (Citron et al., 1996; Strchler-Pierrat et al., 1997), alone or together with the amyloid precursor protein (APP) (Borchelt et al., 1997; Holcomb et al., 1998; Wong et al., 1999), the tau protein (Gotz et al., 1995; Brion et al., 1999) or a βAPP protein C-99 fragment (Jin et al., 1998).

However so far all models develop only some of the morphological, histological or molecular markers defined as characteristic for the diagnosis of Alzheimer's disease and therefore do not represent complete models, effectively suitable to study and provide successful therapies and test drugs. The lack of a comprehensive model for Alzheimer's disease is recognized to represent a crucial bottleneck limiting the screening and validation of new therapeutical agents.

DESCRIPTION OF THE INVENTION

The invention concerns non human transgenic animal, being trangenic for an antibody or fragments thereof and having a phenotype reminiscent of a human pathology.

Preferably the human pathology is included in the following group: neurodegenerative syndromes; muscular atrophy/dystrophy; immune disorders. More preferably the human pathology is the Alzheimer disease (AD).

In an embodiment the non-human transgenic animal exhibits at least one of the anatomical, histological, molecular or phenotypic markers included in the following group: deposition in Central Nervous System (CNS) of plaques of amyloid precursor protein (APP) or of β-amyloid protein, hyperphosphorylation of the tau protein, neurofibrillar pathology, deficits in the cholinergic system.

In a preferred embodiment the non-human transgenic animal of the invention further exhibits at least one of the anatomical, histological, molecular or phenotypic markers included in the following group: glial activation, neuronal loss, cortical and hippocampal atrophy, muscular myositis.

In a more preferred embodiment the non-human transgenic animal of the invention exhibits the following anatomical, histological, molecular or phenotypic markers: deposition in Central Nervous System (CNS) of plaques of amyloid precursor protein (APP) or of β-amyloid protein, hyperphosphorylation of the tau protein, neurofibrillar pathology, deficits in the cholinergic system, glial activation, neuronal loss, cortical and hippocampal atrophy, muscular myositis.

In a most preferred embodiment the non-human transgenic animal of the invention exhibits the anatomical, histological, molecular or phenotypic markers as defined in Table 1 (see below). Preferably the markers are expressed in the adult age.

Another aspect of the invention concerns a non-human transgenic animal wherein the occurrence of the tau hyperphosphorylation and/or the β-amyloid protein deposition in the back or lower limb skeletal muscles and/or the atrophy of said skeletal muscles are present concomitantly to the earliest occurrence of other neurological markers.

A preferred embodiment concerns a non-human transgenic animal according to the invention being transgenic for an anti-NGF (Nerve Growth Factor) antibody or fragment thereof. Preferably the anti-NGF antibody blocks the binding of NGF to its receptors. Preferably the anti-NGF antibody is expressed mainly in the adulthood. Preferably the anti-NGF antibody levels in the serum of the adult animal are comprised between 50 ng/ml and 500 ng/ml. More preferably the anti-NGF antibody is the monoclonal anti-NGF αD11 antibody, most preferably the αD11 antibody is a αD11 chimeric antibody, even more preferably the chimeric antibody is a humanised chimeric antibody.

Preferably the non-human transgenic animal according to the invention is a mammalian, more preferably belonging to the murine genus, most preferably belonging to the *Mus musculus* BS6JL strain.

It is a further object of the invention a method for an early diagnosis of neurodegenerative diseases comprising the monitoring of the occurrence of the tau hyperphosphorylation and/or amyloid deposition in the back or lower limb skeletal muscle sample of a subject.

It is a further object of the invention cells derivable from the non-human transgenic animal of the invention and secreting the transgene antibody. The invention concerns different uses of the cells: for the selection of molecules pharmacologically effective in neurodegenerative and/or muscular pathologies and/or immune disorders; for the grafting in the brain of a non human primate.

Another aspect of the invention relates to a method for the preparation of a non-human transgenic animal comprising essentially the steps of: a) preparing a first non-human transgenic parent animal for the light chain of an antibody and a second non-human transgenic parent animal for the heavy chain of the same antibody, b) breeding the two transgenic parent animals; c) selecting the progeny expressing both the light and the heavy chain. Preferably the antibody is an anti-NGF antibody.

The non-human transgenic animal of the invention can be conveniently used for the study of neurodegenerative syndromes; for the study of pathologies of muscular system; for the study of Alzheimer's disease; for the selection of compounds pharmacologically effective in the treatment of pathologies included in the following group: neurodegenerative syndromes; muscular atrophy/dystrophy, immune disorders; for the selection of compounds pharmacologically effective in the treatment of the Alzheimer's disease; for the study of pathologies related to an NGF deficit; for the screening of compounds potentiating the activity of NGF; for the screening of compounds stimulating the expression and/or the release of endogenous NGF, for the screening of formulations of NGF or derivatives thereof able to cross the blood-brain barrier.

Given that the invention discloses that antibodies anti-NGF can elicit many features of the AD, the invention concerns also the use of NGF or of derivatives or fragments thereof for the preparation pharmaceutical compositions able to bind autoanti-NGF antibodies in the brain of AD affected subjects. The use of NGF or of derivatives or fragments thereof for the preparation of pharmaceutical compositions for the treatment of muscular pathologies is also comprised, as well as pharmaceutical compositions including NGF (Nerve Growth Factor) for the therapy of the muscular pathologies.

DETAILED DESCRIPTION OF THE INVENTION

The present invention describes a non-human transgenic animal able to express an anti-NGF (Nerve Growth Factor) neutralising antibody. The antibody used (αD11) (Cattaneo et al. 1988), binds NGF in correspondence to an epitope responsible for the binding of NGF with its high affinity receptor, TrkA, thus blocking the binding and therefore acting as neutralising antibody. The epitope recognised by the αD11 antibody (comprising the amino acids 41–49 of NGF) corresponds to a poorly conserved sequence in the neurotrophin family and therefore is NGF-specific. Alternatively antibodies able to block the intracellular <<signalling>> pathway, triggered by NGF/TrkA and NGF/p75 interaction, can be used. Alternatively the recombinant antibody can be in the Fab, Fv or single chain Fv form.

Surprisingly the authors of the invention found that transgenic mice for anti-NGF antibodies, which do not express appreciable levels of the antibody in the period immediately after the birth and express such an antibody at levels between 50 and 500 ng/ml in the adult period, develop a complex pathological picture whose characteristic features are:

1) dilation of the cerebral ventricles, symptom often used in clinics as an indication of neurodegenerative diseases, like Alzheimer's disease (Luxenberg et al., 1987);

2) atrophy of the cerebral cortex, sometimes associated with the complete disappearance of the hippocampus;

3) loss of neurons and/or neuronal apoptosis, symptoms related to Alzheimer's disease (Mizutani et al., 1990);

4) deposition in the CNS of plaques of β-amyloid protein, at level of the cerebral cortex, neostriatum, hippocampus;

5) neurofibrillar tangles and dystrophic neurites in the brain;

6) aggregation of the tau protein in the brain.

7) cognitive deficits characterised by defects in the <<working memory>> and spatial orientation deficits;

8) cholinergic deficit;

9) hyperphosphorylation of the tau protein at cerebral level;

10) dystrophy of skeletal muscles, particularly at level of the rear limbs;

11) deposition of plaques of β-amyloid protein in the skeletal muscle;

12) hyperphosphorylation of the tau protein in the muscle;

13) infiltration of inflammatory cells in the muscle;

14) modifications of the sympathetic innervation of the spleen and reduction of the splenocyte viability;

An aspect of the present invention relates to an anti-NGF transgenic animal as a model to study pathologies induced by the NGF deprivation. The NGF deprivation at systemic level can result in various pathologies, even autoimmune.

Surprisingly many characteristics of the transgenic animal model described in the present invention are completely superimposable to those displayed at a macroscopic, histological and molecular level by Alzheimer patients. The present invention therefore provides a non-human transgenic animal model to study Alzheimer's disease. The characteristics of this model are summarised in Table 1 and Table 2, where they are compared with those of other transgenic animals proposed as models for said disease. All the models described in Table 1, except the one described in the present invention, have been derived by overexpression of a wild-type or mutant gene related to AD. Only the anti-NGF model of the instant invention has been obtained with a recombinant antibody as a transgene. As is clear from Table 1, the transgenic animal of the present invention exhibits a comprehensive spectrum of phenotypic markers that, as a whole, have never been previously observed in provided animal models (Hsiao et al. 1996 and WO 95/48792 and WO 97/48792; Citron et al., 1997; Borchelt et al., 1997; Holcomb et al., 1998; Wong et al., 1999; Gotz et al., 1995; Brion et al., 1999; Jin et al., 1998; Games et al., 1995; Irizzary et al. 1997). Table 1 and 2 follow.

TABLE 1

| | Transgenic mice for | | | | | | | | | |
|---|---|---|---|---|---|---|---|---|---|---|
| DEFICIT | APP | Aβ | C-99/C100 Fragment of βPP | PS-1 | PS-2 | APOE | Human Tau | Human Tau (shortest) | Human tau (FTDP-17 mutation) | Anti-NGF antibodies (instant invention) |
| Decreas of cortical thickness | — | | — | — | — | — | — | — | — | + |
| Hippocampal formation Atrophia | +[34] | | — | — | — | — | — | — | — | + |
| Ventricle dilation | — | | — | — | — | — | — | — | +[39] | + |
| Spatial learning deficit | +[4,11,32,37] | — | +[22] | — | — | — | — | — | — | + |
| Neuronal loss | ND[13] +[7,9,10] | — | +[16] | — | — | — | — | — | +[39] | + |
| Apoptosis | +[12,20,37] | +[14] | — | + | — | — | — | ND[27] | — | + |
| β-amyloid plaques | ND[8,9,12,37] +[1–4,7,9,13,32] | ND[33] +[14,35] | +[16,17] | ND[18,21] | +[19] | +[23] | — | ND[27] | — | + |
| Hyperphosphorylated tau | +[1,2,9,32] | — | — | — | — | +[25] | +[26,24,30a,b] | +[27,31a,c] | +[39] | + |
| Neurofibrillary tangles tau aggregates | ND[3,9,12] | — | — | — | — | — | ND[26,30] +[24] | ND[27] +[31a,c] | +[39] | + |
| Dystrophic neurites | +[1–4,9,12,13] | — | +[15] | — | — | +[36] | ND[26,24] | ND[27] | — | + |
| Glial activation | +[3–5,8,9,12,13,37] | +[14] | +[16] | — | — | — | +[30a] | ND[27] | — | + |
| Cholinergic | +[9] | — | ND | — | — | — | — | — | — | + |
| Synaptic loss | +[3,7,34] | +[33] | +[15] | — | — | — | — | — | — | — |
| Synaptic plasticity (decrease) | ND[7] +[6,38] | — | +[16] | — | — | — | — | — | — | + |
| Skeletal muscle atrophia | — | — | +[29] | — | — | — | +[24] | — | — | + |
| Amyloid deposits in skeletal muscles (Congo Red staining) | — | — | +[28] | — | — | — | — | — | — | + |

TABLE 1-continued

| DEFICIT | APP | Aβ | C-99/C100 Fragment of βPP | PS-1 | PS-2 | APOE | Human Tau | Human Tau (shortest) | Human tau (FTDP-17 mutation) | Anti-NGF antibodies (instant invention) |
|---|---|---|---|---|---|---|---|---|---|---|
| Amyloid deposits in skeletal muscles (anti-APP IH) | — | — | +[28] | — | — | — | — | — | — | + |
| Hyperphosphorylated tau (IH) in skeletal muscles | — | — | — | — | — | — | — | — | — | + |
| Inflammation in skeletal muscles | — | — | +[29] | — | — | — | — | — | — | + |
| Vacuolization of myofibers | — | — | +[28] | — | — | — | — | — | — | + |
| Increased number of central nuclei in myofibers | — | — | +[29] | — | — | — | — | — | — | + |

[1] Higgins et al, Ann N Y Acad Sci 1993, 695:224–227.
[2] Higgins et al., Ann Neurol 1994, 35: 598–607.
[3] Games et al., Nature 1995, 373: 523–527.
[4] Hsiao et al., Science 1996, 274: 99–102.
[5] Stalder et al., Am J Pathol 1999, 154: 1673–1684.
[6] Chapman et al., Nat Neurosci 1999, 2: 271–276.
[7] Hsia et al., Proc Natl Acad Sci USA 1999, 3228–3233.
[8] Hsiao et al., Neuron 1995, 15: 1203–1218.
[9] Sturchler-Pierrat et al., Proc Natl Acad Sci USA 1997, 94: 13287–13292.
[10] Calhoun et al., Nature 1998, 395: 755–756.
[11] Moran et al., Proc Natl Acad Sci USA 1995, 92: 5341–5345.
[12] Moechars et al., Behav Brain Res 1998, 95: 55–64.
[13] Irizzary et al., J Neurosci 1997, 17: 7053–7059.
[14] LaFerla et al., Nat Genet 1995, 9: 21–30.
[15] Oster-Granite et al., J Neurosci 1996, 16: 6732–6741.
[16] Nalbantogiu et al., Nature 1997, 387: 500–505.
[17] Kammersheidt et al., Proc Natl Acad Sci USA 1992, 89: 10857–10861.
[18] Duff et al., Nature 1996, 383: 710–713.
[19] Oyama et al., J Neurochem 1998, 71: 313–322.
[20] Moechars et al., Neuroscience 1999, 91: 819–830.
[21] Chui et al., Nat Med 1999, 5: 560–564.
[22] Berger-Sweeney et al., Brain Res Mol Brain Res 1999, 66: 150–162.
[23] Holtzmann et al., J Clin Invest 1999, 103: R15–R21.
[24] Probst et al., Acta Neuropathol 2000, 99: 469–481.
[25] Tesseur et al. Am J Pathol 2000, 156: 951–964.
[26] Gotz et al., EMBO J 1995, 14: 1304–1313.
[27] Brion et al., 1999, 154: 255–270.
[28] Fukuchi et al., Am J Pathol 1998, 153: 1687–1693.
[29] Jin et al., Am J Pathol 1998, 153: 1679–1686.
[30] Spittaels et al., Am J Pathol 1999, 155: 2153–2165.
[31] Ishihara et al., Neuron 1999, 24: 751–762.
[32] Moechars et al., J Biol Chem 1999, 274: 6483–6492.
[33] Mucke et al., J Neurosci 2000, 20: 4050–4058.
[34] Dodart et al., Neurobiol Dis 2000, 7: 71–85.
[35] Shoji et al., J Pathol 2000, 191: 93–101.
[36] Holtzmann et al., Proc Natl Acad Sci USA 2000, 97: 2892–2897.
[37] Kumar-Singh et al., Neurobiol Dis 2000, 7: 9–22.
[38] Larson et al., Brain Res 1999, 840: 23–25.
[39] Lewis et al., 7th International Conference on Alzheimer's Disease and Related Disorders, abstr. 269.
— not reported
ND not detected
[a] reported mainly in the spinal cord
[b] reported mainly in axons
[c] reported mainly in young animals (<9 months of age)

TABLE 2

| DEFICIT | APP and PS-1 | APP and APOE | APPCRND 8 and PS2 | APPCRND 8 and PS1 | APP and PS1 and TAU | APP and TAU4R | Anti-NGF antibody (instant invention) |
|---|---|---|---|---|---|---|---|
| Decrease of cortical thickness | — | — | — | — | — | — | + |
| Hippocampal formation atrophia | — | — | — | — | — | — | + |
| Ventricle dilation | — | — | — | — | — | — | + |
| Spatial learning deficit | $+^{3,8,16}$ | — | $+^{21}$ | — | — | — | + |
| Neuronal loss | $ND^1$ | — | — | — | — | — | + |
| Apoptosis | — | — | — | — | — | — | + |
| β-amyloid plaques | $+^{1-5,7,9,11,14,15}$ | $+^{19,20}$ | $+^{21,22}$ | $+^{22}$ | $+^{23}$ | $+^{24}$ | + |
| Hyper-phosphorylated tau | $+^{10}$ | — | — | — | $+^{23}$ | $+^{24}$ | + |
| Neurofibrillary tangles tau aggregates | — | — | — | — | — | — | + |
| Dystrophic neurites | $ND^1$ | — | — | — | — | $+^{24}$ | + |
| Glial activation | $+^{9,12}$ | — | — | — | — | — | + |
| Cholinergic deficit | $+^{6,17}$ | — | — | — | — | — | + |
| Synaptic loss | $+^{7,13}$ | — | — | — | — | — | — |
| Synaptic plasticity (decrease) | $+^{18}$ | — | — | — | — | — | + |

[1] Borchelt et al., Neuron 1997, 19: 939–945.
[2] Citron et al., Nat Med 1997, 3: 67–72.
[3] Holcomb et al., Nat Med 1998, 4: 97–100.
[4] Lamb et al., Nat Neurosci 1999, 2: 695–697.
[5] Borchelt et al., Neuron 1996, 17: 1005–1013.
[6] Wong et al., J Neurosci 1999, 19: 2706–2716.
[7] Takeuchi et al., Am J Pathol 2000, 157: 331–339.
[8] Holcomb et al., Behav Genet 1999, 29: 77–85.
[9] McGowan et al., Neurobiol Dis 1999, 6:231–244.
[10] Howlett et al., 7th International Conference on Alzheimer's Disease and Related Disorders,abstr. 1021.
[11] Dewatcher et al., 7th International Conference on Alzheimer's Disease and Related Disorders,abstr. 91.
[12] Matsuoka et al., 7th International Conference on Alzheimer's Disease and Related Disorders,abstr. 84.
[13] Kadish et al., 7th International Conference on Alzheimer's Disease and Related Disorders,abstr. 396.
[14] Czech et al., 7th International Conference on Alzheimer's Disease and Related Dlsorders,abstr. 90.
[15] Moussaoui et al., 7th International Conference on Alzheimer's Disease and Related Disorders,abstr. 89.
[16] Morgan et al., 7th International Conference on Alzheimer's Disease and Related Disorders,abstr. 83.
[17] Hu et al, 7th International Conference on Alzheimer's Disease and Related Dlsorders,abstr. 401.
[18] Kuenzi et al., 7th International Conference on Alzheimer's Disease and Related Disorders,abstr. 563.
[19] Holtzmann et al., J Clin Invest 1999, 103:R15–R21.
[20] Bales et al., Proc Natl Acad Sci USA 1999, 96: 15233–15238.
[21] Janus et al., 7th International Conference on Alzheimer's Disease and Related Disorders,abstr. 564.
[22] Chishti et al., 7th International Conference on Alzheimer's Disease and Related Disorders,abstr. 568.
[23] Duff et al., Neurobiol Dis 2000, 7: 87–98.
[24] Tolnay et al., 7th International Conference on Alzheimer's Disease and Related Disorders,abstr. 875.
— not reported
ND = not detected Table 2 illustrates the phenotypic markers in transgenic mice derived by crossing two lines of mice with different transgenes (double transgenic models), in comparison to the anti-NGF mice. Also in this case, the spectrum of alterations found in the anti-NGF mice is far more extensive and comprehensive than in other models.

Thus it is clear that the transgenic animal of the present invention constitutes a much more complete animal model for Alzheimer's disease than those available by the prior art. As a matter of fact, deficits present in the anti-NGF mouse, resulting from the expression of the transgenic antibodies, are at level of both central and peripheral nervous system, at cognitive level, at muscle level and further at morphological-functional level in the spleen, wherein anomalies in the immunoglobulin expression pattern can be found. In this regard the ever-increasing experimental evidences indicating as central the role played by the immune system in the development of Alzheimer's disease are very interesting (Kalaria, 1993).

The preparation of the transgenic animal is carried out by breeding of two lines of parent transgenic mice which are transgenic for the heavy and the light chain of an anti-NGF antibody, respectively, and such a method of preparation is a further aspect of the present invention. The two lines of the parent transgenic animals are prepared by microinjection of plasmid DNA in ES cells or in the oocyte fecundated according to standard methods known by those skilled in the art.

The plasmid vectors containing the transcription units for the cDNA expression of both immunoglobulin chains are purified, for example by banding technique using a CsCl continuous gradient, then diluting with physiological saline. The vectors can be injected as such in the pro-nucleus of fecundated oocytes, or can be made linear by enzymatic restriction in a unique site or the transcription units can be separated from the vector by enzymatic restriction, purified, for example by gel electrophoresis or ion exchange chromatography, and separately introduced in the pronuclei. Preferably murine oocyte is used, more preferably it is from the B6SJL strain. The two immunoglobulin chains of the anti-NGF antibody can be chimeric, obtained by assembling the variable murine regions of an ant-NGF monoclonal antibody, like Mab αD11, having human constant regions of K light and γ1 heavy chains, as described in the present invention or derived as such from the specific cDNA of the secreting hybridoma. The expression of the two antibody chains in the trangenic mouse is controlled by a strong viral promoter, as CMV-IE (Cytomegalovirus Immediate Early), which is expressed ubiquitously. Other ubiquitous promoters which can be used are RSV (Rous Sarcoma Virus) LTR, or SV40 (SV40-IE) early gene promoters. According to a further embodiment of the invention, in order to modulate the expression of the correctly assembled and functional antibody only in particular districts of the organism the two transgenes can be brought under the control of two different promoters. In order to express the functional antibody only in a particular district or control the same over the time, can be used however tissue-specific or inducible promoters which can be different for the two antibody chains.

The preparation of the transgenic animal carried out according to the method of the invention determines the expression of the functional antibody in the adult transgenic animal at levels about 2000 times higher than at the birth and this allows, on one hand, according to the method of the invention, to increase up to 80% the efficiency in the production of viable transgenic brood for both antibody chains, and on the other hand to express the phenotype resulting from the NGF activity only in the adult period, avoiding its neutralisation during the neuronal differentiation.

The transgenic mice obtained according to the method of the invention are able to express, at different level and in any case at amounts in the range from 50 to 500 ng/ml of serum, the functional chimeric antibody consisting of both the correctly assembled and secreted chains and said transgenic mice do not produce a lethal phenotype during the first post-natal period, as opposed to the transgenic animal obtained by microinjecton of the plasmids encoding for both the immunoglobulin chains in the same oocyte.

Time course experiments on the development of the neurodegenerative phenotype in the transgenic mice described in this invention reveal that, in the brain, the first signs of neurodegeneration are a cholinergic deficit and modification of some cytoskeletal proteins (2 months of age). The experiments of the authors of the invention pointed out that, in the periphery, the earliest signs of neurodegenerative pathology at the brain level are concomitant to an early (2 month age) tau hyperphosphorylation and amyloid deposition in the back or lower limb skeletal muscles. It is therefore within the scope of the present invention the use of the skeletal muscle monitoring for an early diagnosis of neurodegenerative diseases.

Further it is pointed out that the muscular system phenotype of the anti-NGF mouse can be reversed by NGF local administration. According to its further aspect, the invention therefore is directed to the use of NGF for the preparation of pharmaceutical compositions to be used for the therapy of muscular pathologies, as muscular dystrophy/atrophy. The administration of said neurotrophin can be carried out by different routes among which there are: intramuscular injection of NGF, for example recombinant NGF, dissolved in suitable physiological saline, or direct injection of plasmid or recombinant viral vectors, for example adenovirus, or by implant in the muscle of cells genetically engineered for the NGF secretion. The dose can depend on various variables as the specific activity of the protein, severity of the pathology to be treated, general conditions of the patient and in any case will be form 2 to 100 μg/kg of body weight.

Further it is found that the cholinergic deficit and the tau hyperphosphorylation in the cortex are reversed by direct infusion of NGF, or by infusion of agents that increase the production of NGF in the brain. Moreover, the neurodegenerative phenotype is reversed by intraventricular infusion of a phage particle displaying a peptide recognized by the anti NGF aD11 antibody.

DESCRIPTION OF FIGURES

FIG. 7 Neuronal apoptosis Tunel labeling of apoptotic cortical neurons. In control mice (A) there is no positivity, while in anti-NGF mice (B) there are many nuclei with DNA fragmentation.

FIG. 8 Phosphorilation of tau protein Transgenic mice show a marked positivity for the N-terminal segment of tau protein (B), non phosphorylated tau (D) and hyperphosphorylated tau (F). In control mice there is no labeling (A,C,E). Labeling is localized in the cortex (E). Labeling for the N-terminal segment of protein tau in localized in some cells of the hippocampus (arrows).

EXAMPLE 1

Figure 1:
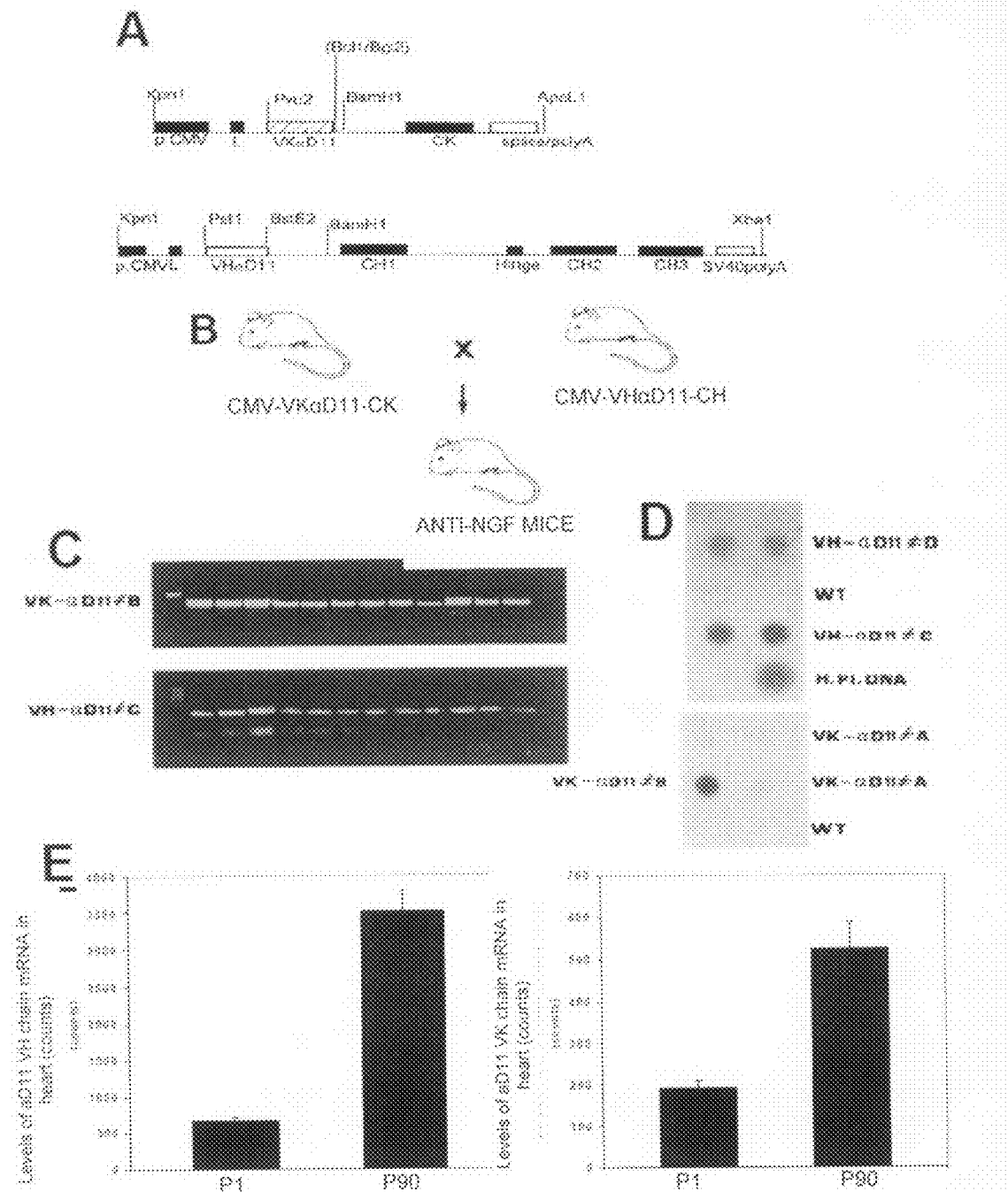
FIG. 1. Production of anti-NGF transgenic mice. (A) DNA constructs for the production of the transgenic mice: light chain (upper panel) and heavy chain (lower panel) transgenes. CK and CH1–CH3, human constant region domains of light (K) and heavy (γ1) chains; VK and VH, light and heavy chain variable regions of the αD11 monoclonal antibody; CMV, cytomegalovirus promoter. (B) Crossing mice to generate mice expressing the functional anti-NGF antibody. VK-αD11×VH-αD11 (VK: line of mice expressing the light chain of αD11 antibody; VH: line of mice expressing the heavy chain of αD11 antibody) (C) PCR analysis to detect the presence of VK (upper panel) and VH (lower panel) transgenes. The gels show 12 littermates born from homozygous VK (upper panel) or VH (lower panel) mice crossed to negative mice, to verify homozygosis of the single transgenic lines. As evident, all littermates carry the transgene. (D) Dot blot analysis of the four lines of mice expressing the heavy or the light chain. The upper panel was probed with a human heavy chain constant region probe and the lower panel with a human light chain constant region probe (see Methods). DNA samples in the upper panel: duplicates of VH-αD11 #D, wild type (WT, negative control) and VH-αD11 #C, single sample of human placental DNA (H.PI.DNA, positive control). DNA samples in the lower panel: duplicate of VK-αD11#A, single samples of VK-αD11#B, WT (negative control), and Human placental DNA (positive control). (E) Levels of VH-αD11 (left panel) and VK-αD11 (right panel) mRNA in heart at P1 and P90 of mice from family #1, evaluated by phosphorimaging analysis, normalized to the β-actin mRNA (mean counts±SEM). (F) Levels of mRNA for the VH-αD11 chain (left panel) and the VK-αD11 chain (right panel) in heart at P1 and P90 of mice from family 1, evaluated by phosphorimaging analysis, normalized to the β-actin mRNA (mean counts±SEM). Number of mice for each age, n=6.

Production of Anti-NGF Transgenic Mice and Molecular Characterisation

Transgene Preparation

The recombinant chimeric antibody was obtained by assembling the sequences of DNA corresponding to the murine variable regions of the Mab αD11 anti-NGF monoclonal antibody (Ruberti et al., 1993) (Genebank, access numbers: L17077/NID g310168: heavy chain and L17078/g310169: light chain, respectively) with the DNA corresponding to the constant regions of the human light K and heavy γ1 chains. Transcription units, corresponding to the chimeric light and heavy chains (FIG. 1A), containing at 5'end the Cytomegalovirus promoter and at 3'end the polyadenylation site of the bovine growth hormone (bGH), were cloned into the expression vectors pcDNAI-NeoVKαD11HuCK and pcDNAI-NeoVHαD11HuCγ, respectively. Then they were extracted using KpnI-ApaI and KpnI-XbaI restriction enzymes, respectively, purified and injected separately or in combination in the pro-nucleus of mouse B6SJL strain egg cells fecundated according to standard methods (for example see Allen et al., 1987). Two transgenic parents for the light (A and B family, low and high producer, respectively), two for the heavy (C and D family, low and high producer, respectively) and three for both (double transgenic) antibody chains were obtained, respectively. The latter parents, which express the antibody at a level of about 50 ng/ml, are unable to reproduce and therefore are unsuitable for the continuation of the study.

The molecular analysis of the transgenic parent mice (A, B, C and D families) was carried out by PCR (FIG. 1C) or Dot Blot (FIG. 1D) on genomic DNA extracted from tail biopsies as described in Piccioli et al., 1995. mRNA was extracted according to Chomcynzki and Sacchi, 1987, at different times form the birth and was analysed by RNAse-protection.

Preparation of the Anti-NGF Mouse

In order to generate transgenic animals for the functional antibody, consisting of both chains, two transgenic parents for the light (parents A and B) or for the heavy (parents C and D) chains were bred in different combinations (FIG. 1B). Only breeding of A with D and B with C parents, which result in families 1 and 2 of double transgenic heterozygotic mice, αD11 anti-NGF monoclonal antibody (Ruberti et al., 1993) (Genebank, access numbers: L17077/NID g310168: heavy chain and L17078/g310169: light chain, respectively) with the DNA corresponding to the constant regions of the human light K and heavy γ1 chains. Transcription units, corresponding to the chimeric light and heavy chains (FIG. 1A), containing at 5'end the Cytomegalovirus promoter and at 3'end the polyadenylation site of the bovine growth hormone (bGH), were cloned into the expression vectors pcDNAI-NeoVKαD11HuCK and pcDNAI-NeoVHαD11HuCγ, respectively. Then they were extracted using KpnI-ApaI and KpnI-XbaI restriction enzymes, respectively, purified and injected separately or in combination in the pronucleus of mouse B6SJL strain egg cells fecundated according to standard methods (for example see Allen et al., 1987). Two transgenic parents for the light (A and B family, low and high producer, respectively), two for the heavy (C and D family, low and high producer, respectively) and three for both (double transgenic) antibody chains were obtained, respectively. The latter parents, which express the antibody at a level of about 50 ng/ml, are unable to reproduce and therefore are unsuitable for the continuation of the study.

The molecular analysis of the transgenic parent mice (A, B, C and D families) was carried out by PCR (FIG. 1C) or Dot Blot (FIG. 1D) on genomic DNA extracted from tail biopsies as described in Piccioli et al., 1995. mRNA was extracted according to Chomcynzki and Sacchi, 1987, at different times form the birth and was analysed by RNAse-protection.

Preparation of the Anti-NGF Mouse

In order to generate transgenic animals for the functional antibody, consisting of both chains, two transgenic parents for the light (parents A and B) or for the heavy (parents C and D) chains were bred in different combinations (FIG. 1B). Only breeding of A with D and B with C parents, which result in families 1 and 2 of double transgenic heterozygotic mice, respectively, are fertile and generate viable animals with an over 80% efficiency.

Characterisation of the Anti-NGF Mouse

The levels of the functional antibody of either light or heavy chains of the transgenic animals were measured by ELISA assays (Monlar et al., 1998), using a biotin labelled human anti-IgG secondary antibody, after 1:10 dilution of serum or brain homogenates (Piccioli et al., 1995) with PBS-2% powder milk.

The levels of the anti-NGF chimeric antibody for families 1 and 2, measured in the serum and in cerebral tissue of adult animals (90 day-old) are higher than 100 ng/ml and 100 ng/mg, respectively. The values for family 2 are about two times higher than those for family 1. Soon after birth (1 day) the antibody levels are lower than the detection limit of the assay (0.1 ng/ml in the serum and 0.1 ng/ml in the tissues) (FIG. 2C).

mRNAs specific for the chimeric VH and VK chains are expressed in different tissues among which brain, kidney, heart, muscle, liver and testicles. mRNA levels of both chains in the adult (90 day old) are about six times higher than in the newborn animal (1 day) (FIG. 1 E).

Therefore the high expression (1–2000×) of the anti-NGF functional antibody observed in the heterozygotous animal (double transgenic) is only partially due to the increase of mRNA levels.

Organ sections of anti-NGF mice are fixed by intracardiac perfusion of 4% paraformaldehyde in PBS, collected on a slide, preincubated in 10% foetal serum and 5% BSA, then used to detect by immunohistochemistry the expression of different antigens: particularly the co-expression of the light and heavy chains of the anti-NGF antibody were made detectable by biotinylated anti-human light or heavy chain (Amhersham), detected by HRP or AP-conjugated avidin-biotin (Elite Standard kits, Vector). The localisation at cerebral level is showed in FIG. 2A, while in FIG. 2B is revealed by immunohistochemistr, demonstrating that the two chains of the chimeric antibody are co-expressed frequently.

EXAMPLE 2

NGF Phenotype Knockout in Anti-NGF Transgenic Mouse

Figure 2:
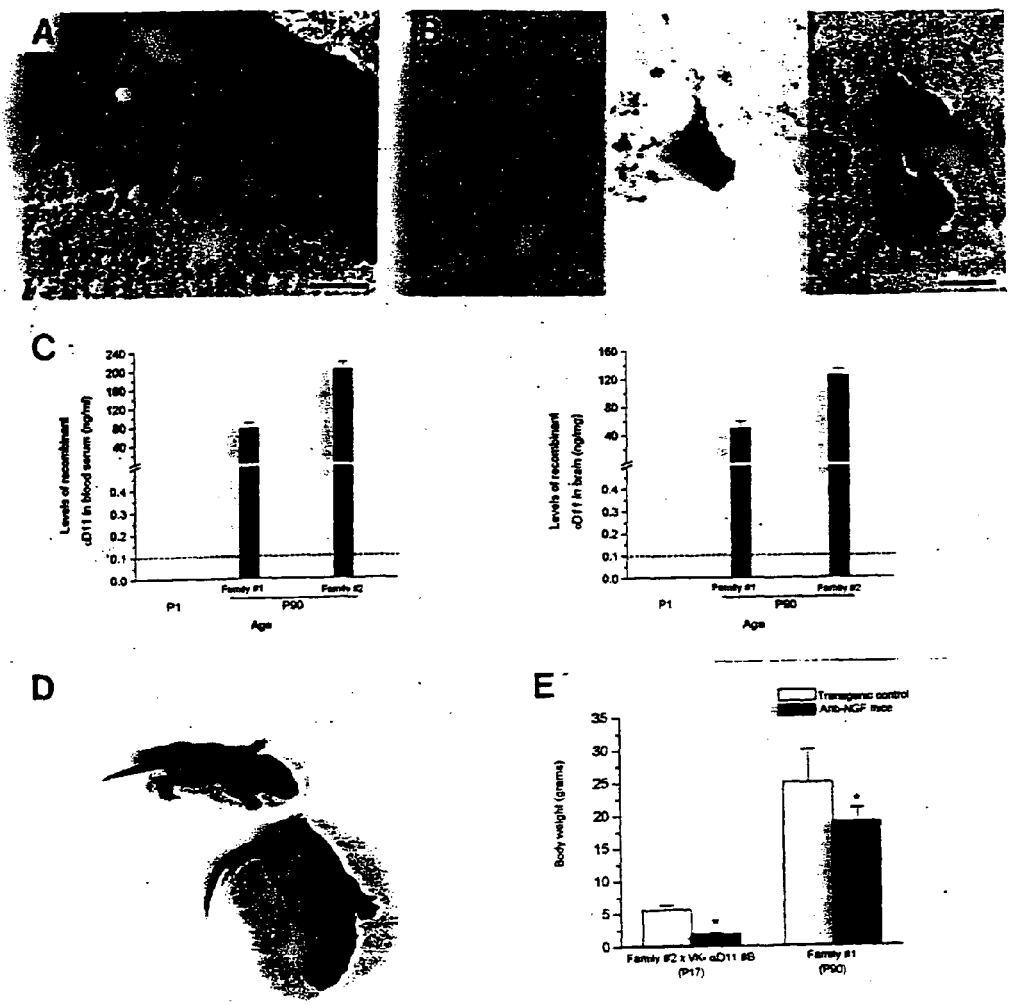
FIG. 2. Expression of functional antibodies in anti-NGF transgenic mice. (A) Expression of the recombinant VH in Purkinje cells of the cerebellum of VH-αD11 #C mice. Scale bar=38 μm. (B) Expression of VH (left) and VK (center) chains, in DRG (Dorsal root ganglia) of family #1 mice. The coexpression of the two chains in the same cells is shown in the right panel Scale bar: 25 μm. (C) Level of recombinant αD11 in the serum (left) and in the brain (right) of family #1 and family #2 mice, at P1 and P90. The horizontal dotted line represents the detection threshold of the assay (0.1 ng/ml). (D) A transgenic control (transgenic for VH only) and a transgenic anti-NGF (family #3) mouse at P17. The transgenic mouse is much smaller than the control. (E) Body weight in anti-NGF mice (family #1 and family #2) (left) and transgenic control (right).

The characterisation of the anti-NGF mouse phenotype was carried out at different levels: macroscopic, histological and molecular. At macroscopic level, during the first 3–4 life weeks anti-NGF transgenic mice do not show remarkable abnormalities, except an about 25% decrease of body weight compared to corresponding control mice (FIG. 2 D and E). Usually experiments were carried out on anti-NGF transgenic animal of numerosity group n=6 with anti-NGF antibody levels from 50 to 300 ng/ml; as controls transgenic mice were used only for the antibody heavy chain (VH) (parent C or D), therefore not expressing the functional antibody.

At histological and molecular level the following differences, compared to normal mice, were observed, district by district: 1) central and peripheral nervous system, 2) muscular system and 3) spleen.

1) Central and Peripheral Nervous System

Figure 3:
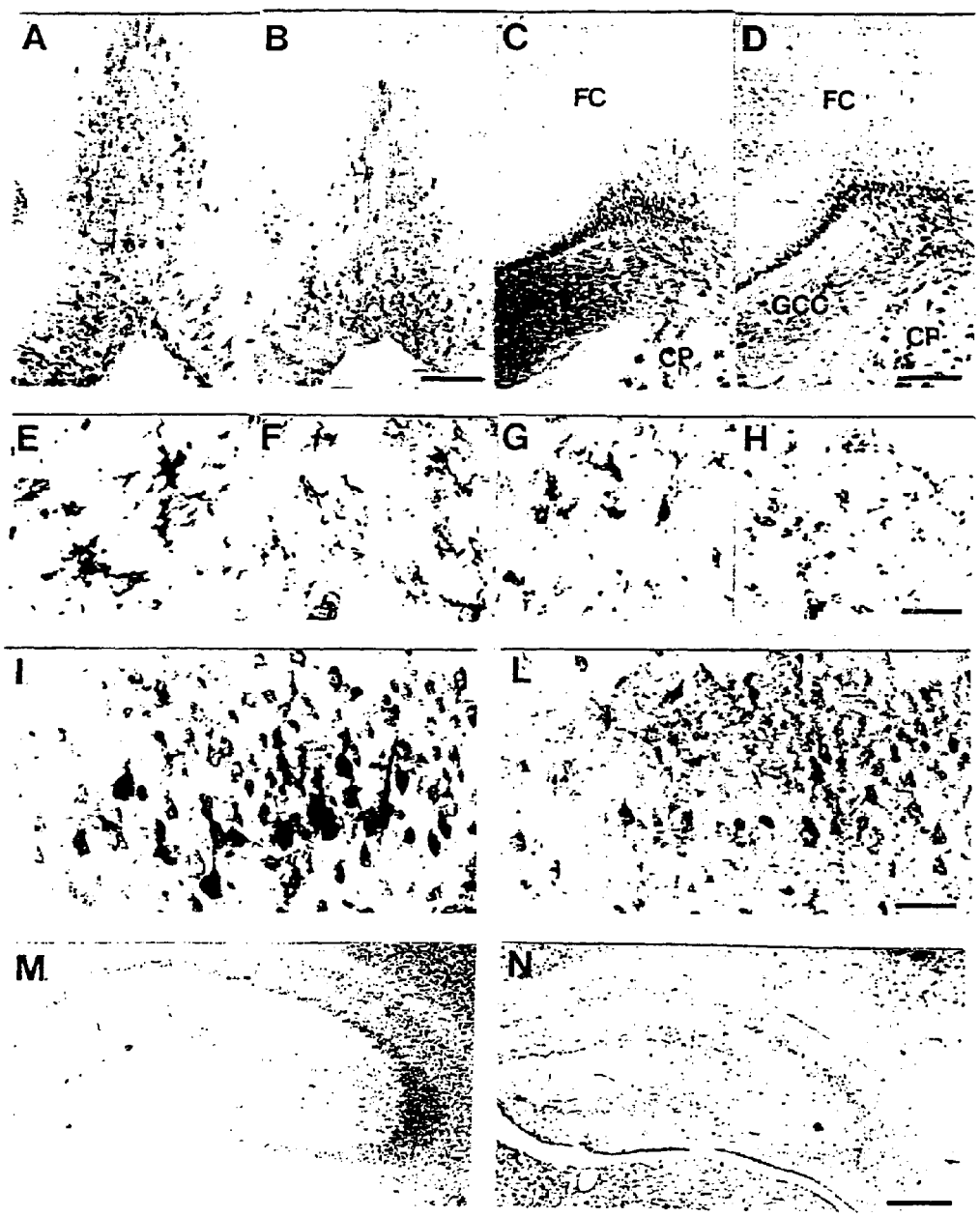
FIG. 3. Phenotypic analysis of the central nervous system of anti-NGF transgenic mice A–H: Sections through the basal forebrain BF: CHAT-positive neurons in control (A) and anti-NGF transgenic mice (B). Cholinergic innervation to the frontal cortex, stained with anti-ChAT, in control (C) and anti-NGF transgenic mice (D). CP: caudate/putamen; FC: frontal cortex; GCC: genus corpus callosum. TrkA-positive neurons of the BF in control (E) and anti-NGF transgenic mice (F). p75-positive neurons in the BF of control (G) and anti-NGF transgenic mice (H). CHAT staining of hippocampal section in control (I) and anti-NGF transgenic mice (L). Timm's staining in hippocampal mossy fibers of control (M) and anti-NGF transgenic mice (N). Scale bar in (A–D; M–N)=300 µm; (E–H)=150 µm; (I–L) =38 µm. The figures are representative of an analysis performed on 10 animals for each group.

In the basal forebrain a reduction up to 57% in the number of acetyltransferase-positive neurons (ChAT) and a reduction of the expression level were observed, while in the hippocampus a reduction up to 70% of neurons is observed. In addition cells appear morphologically smaller. As to the peripheral nervous system the upper cervical ganglia are up to 45% smaller than control; also in this case cells appear morphologically smaller (FIGS. 3 A–B). The morphological and histological aspect of mouse brain expressing the anti-NGF recombinant antibody was analysed in transgenic 15–18 month-old mice (<<aged>> animals), in combination with the presence of phenotypic markers of neurodegenerative diseases, as following: <<neuronal loss>> and apoptosis, expression of choline-acetyltransferase (ChAT) (FIG. 3

A, B), determined by immunohistochemistry with anti-ChAT anti-serum (Chemicon International, Temecula Calif., USA), ratio of phosphorylated to non phosphorylated tau protein (measured by immunohistochemistry or western blot with specific antisera), presence of β-amyloid protein and of amyloid precursor protein (APP), (determined by immunohistochemistry with specific antisera). The numerosity of the groups used for the experiments, except where otherwise indicated, was n=6 transgenic anti-NGF with transgenic anti-NGF antibody levels from 50 to 300 ng/ml; as control were used mice transgenic only for the antibody heavy chain (VH) (parent C and D), therefore not expressing the functional antibody.

Figure 4:
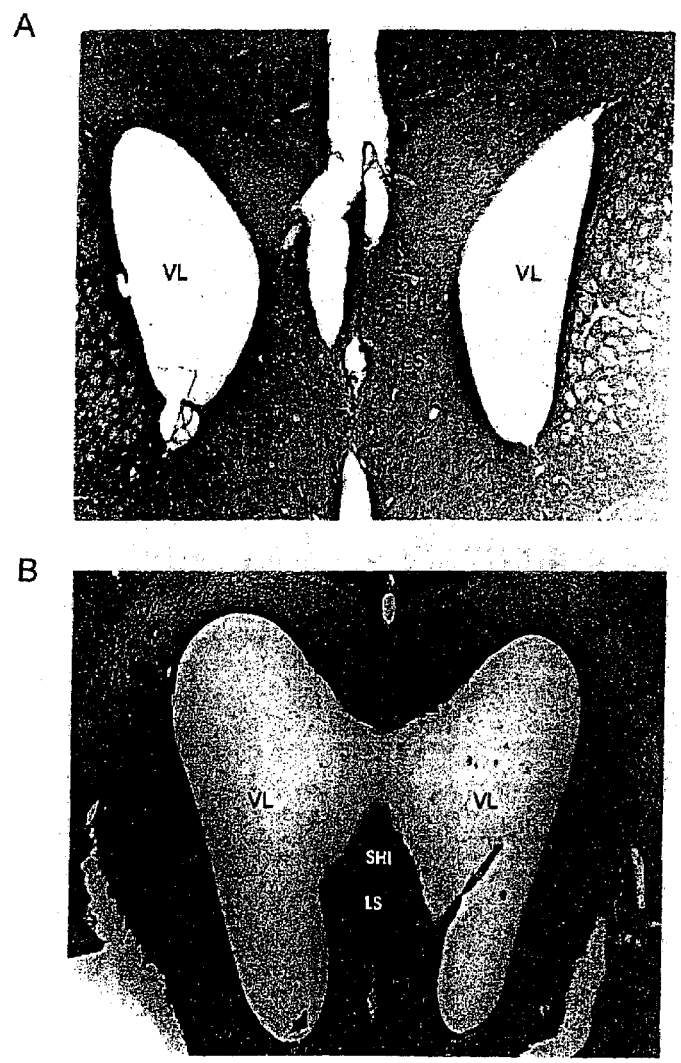
FIG. 4 Dilation of lateral cerebral ventricles Coronal sections stained with the cresyl violet method. Aged anti-NGF mice show dilation of lateral ventricle s(VL) (B) with respect to control mice (A). It has been observed the atrophy of the septohippocampal nuclei (SHI) and of lateral septal nuclei (LS).
Figure 5C:
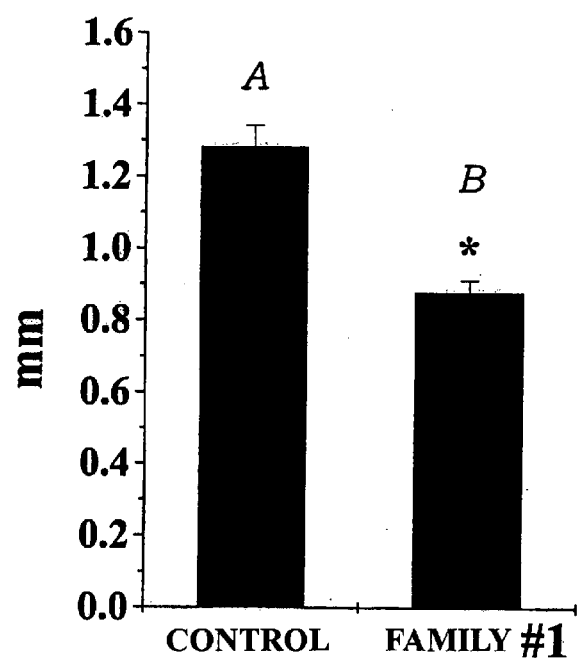
FIG. 5 Atrophy of the cerebral cortex Coronal sections obtained at the level of the basal forebrain. The frontal cortex is atrophic in anti-NGF mice (B) with respect of to control mice (A). The white bar indicates the thickness measured in the anatomical region. (C) Histogram comparing the status in transgenic (B) with respect to control (A) mice.
Figure 6C:
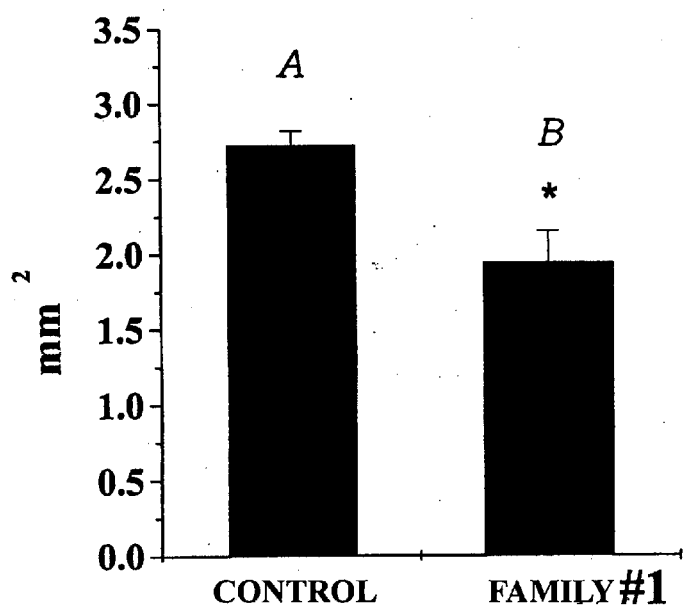
FIG. 6 Atrophy of the hippocampus. In control mice hippocampi (Hp) are normal (A) with respect to transgenic mice (B). (C) Histogram comparing the status in transgenic (B) with respect to control (A) mice.

Results can be summarised in the following points:

(a) Dilation of cerebral ventricles (FIG. 4). The severity of the ventricular dilatation is associated to a remarkable atrophy of the cerebral cortex (FIG. 5) and hippocampus (FIG. 6).

Figure 7:
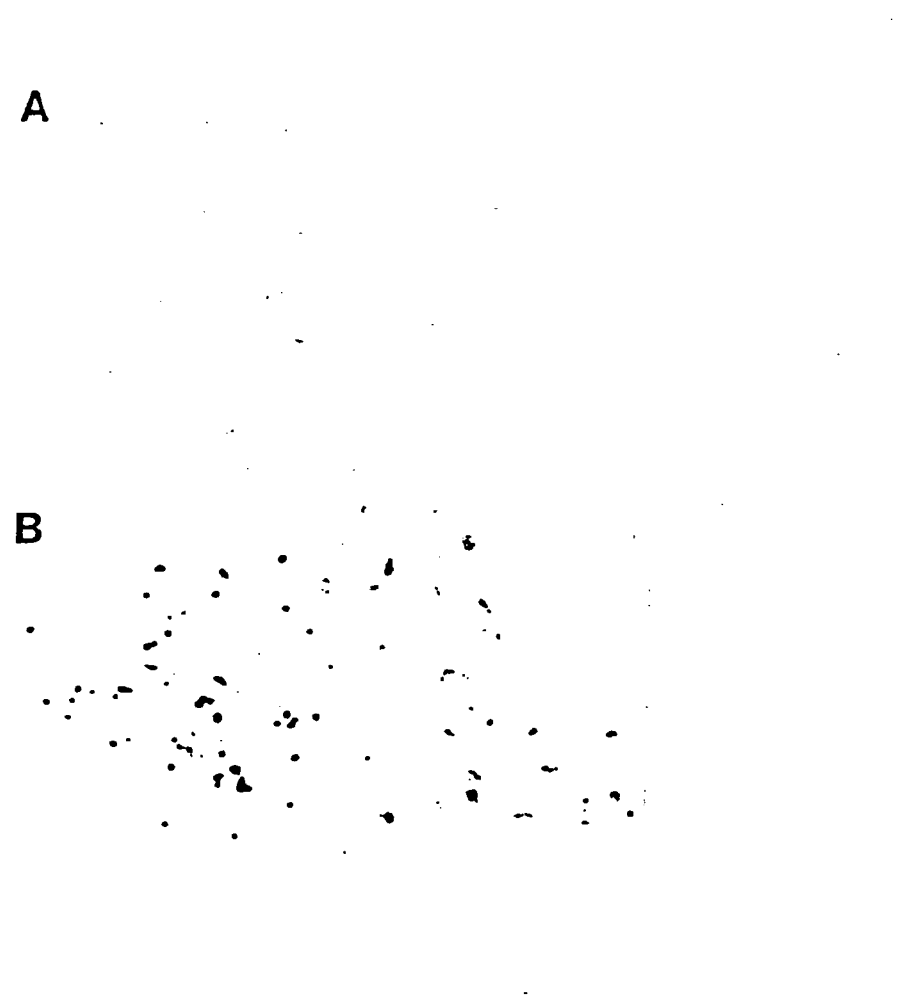

(b) Neurodegeneration and neuronal loss. It is possible to visualise apoptotic cells in more severely damaged mice at cerebral level as pointed out by the TUNEL method (FIG. 7). Apoptotic phenomena indicate a progressive cell death.

(c) Decrease of choline-acetyltransferase (ChAT) synthesis, (FIG. 3 A–B and I–L), particularly in the basal forebrain. Namely no neurons positive for this marker in the nucleus of the medial septum are observed in analysed animals. The expression, when compared to that observed in younger (2–3 month-old) mice, is decreased. A lower expression is also observed for the two NGF-receptors, TrkA (FIG. 3 E–F) and p75, in the basal forebrain (FIG. 3 G–H). Particularly the decrease for the TrkA-positive is more remarkable than for p75-positive cells.

(d) Increase of the phosphorylation of tau protein (FIG. 8). Using antibodies specific for the N-fragment of the tau protein [Alz-50 (Wolozin et al., 1986)] (FIGS. 8A and 8B), for the unphosphorylated tau protein [anti-Tau 1 (Grundke-Ipbal et al., 1986)] (FIGS. 8C and 8D), or for the same epitope of the phosphorylated tau protein [mAB AT-8 (Greenberg and Davies, 1990)] (FIGS. 8E and 8F), a remarkable generalised increase of the tau synthesis, mainly of the phosphorylated component thereof, was detected by immunochemical methods. Used antibodies label cortical neurons which present a modified morphology, evidencing the presence of <<neuropil threads>>, <<ghosts>> and <<tangles>>. The labelling of the phosphorylated form of tau protein evidenced a remarkable increase of this protein also in the microglial cells which are activated in neurodegenerative processes.

Figure 10:
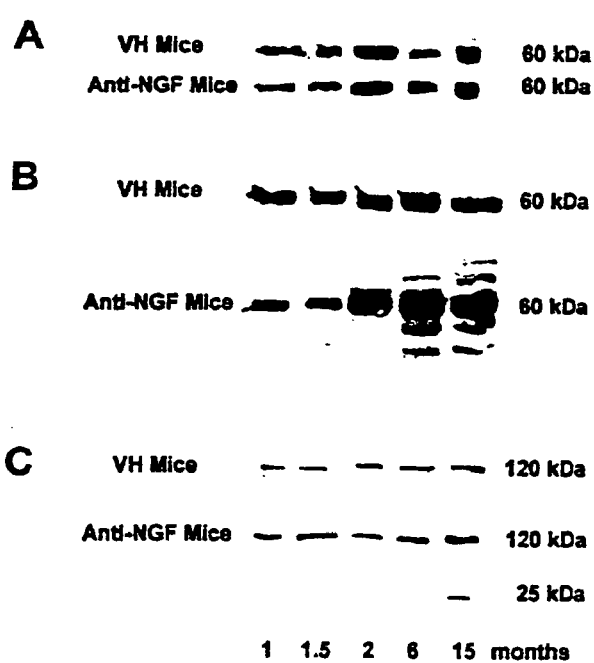
FIG. 10 Western blot of brain extracts from anti-NGF and control mice Western analysis of brain extracts from anti-NGF and control mice. Blots were probed with mAbs YOL1 (anti-tubulin, as provided by Dr. Cesar Milstein) (A), AT8 (anti-phosphorylated tau) (B) and anti-APP(C). Blots are representative of 3 different experiment in which at least 3 control and 3 anti-NGF mice for each age were used. In each panel upper and lower rows represent blots from extracts derived from control and anti-NGF mice, respectively.

In a further experiment the progressive increase of the hyperphosphorylated tau content in the brain of the anti-NGF mice was evaluated by biochemical analysis (Western blot analysis). Results were normalised for the total protein content using an antibody against tubulin (FIG. 10A). The western blot analysis carried out using the antibodies against hyperphosphorylated tau (PHF-1 and AT-8) demonstrated that an increase of the phosphorylated tau content is present in 2 month-old animals and the tau content reaches a plateau 6 months after birth (FIG. 10B). The biochemical analysis of the amyloid precursor protein demonstrated that the content of this protein increases from 6 months after birth (FIG. 10C). Furthermore 15 months after birth two bands, corresponding to 120 kDa and 25 kDa, respectively, are observed (FIG. 10C).

Figure 11:
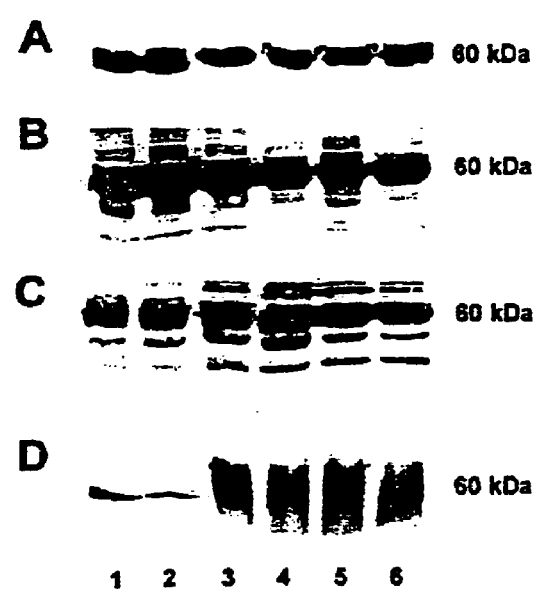
FIG. 11 Accumulation of tau Protein in the brain of anti-NGF transgenic mice. Insoluble tau protein accumulates in the brain of 15 months-old mice. Protein amount was checked using anti-tubulin antibodies (A). Tissues were sequentially extracted with RAB Hi-salt (B), RIPA buffer (C) and 70% FA (D). RAB-insoluble tau, represented by the RIPA and FA fractions, accumulates in the brain of anti-NGF mice but not in control mice. B, C, and D were visualized with anti-tau antibodies 7.51. Lanes 1–2 refer to controls; lanes 3–5 to anti-NGF mice.

The presence of insoluble aggregates of tau protein was evaluated in 15 month-old anti-NGF mice. Brains were extracted sequentially using buffers with different extraction activity. Experiments evidenced that in the anti-NGF mice most hyperphosphorylated tau protein is insoluble (FIG. 11).

Therefore the modification at the protein level of the tau cytoskeleton precedes the modifications observable at the amyloid protein level. Further the experiments evidence the presence of insoluble tau, which can be part of that component forming PHFs (paired helical filaments) which constitute the intracellular tangles and extracellular deposits in the Alzheimer disease. The results show a modified processing of the amyloid protein too.

Figure 9:
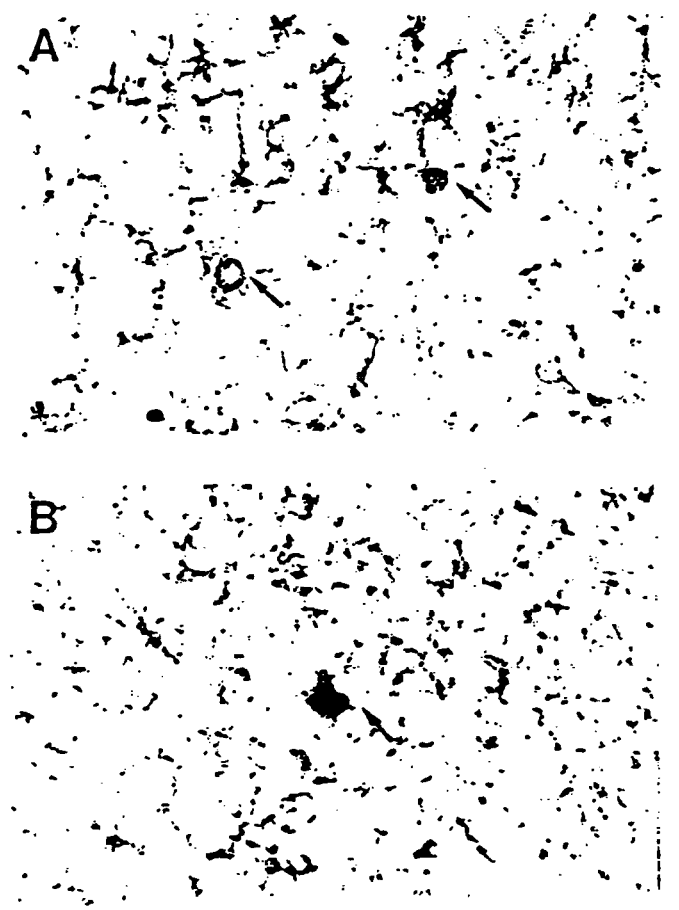
FIG. 9 Deposition of β-amyloid protein plaques in the brain The antibody MN10 and the antibody against the amyloid precursor protein show plaques in control mice (A) and bigger plaques in transgenic mice (B). In both figure arrows point to plaques.

(e) Amyloid plaques in the brain of 15 month-old anti-NGF transgenic mice. In another experiment the presence of amyloid plaques was detected using antibodies against the β-amyloid protein (4G8, Sentek, Md. Heights, Mo.) and against amyloid precursor protein [APP (Glenner and Wong, 1984) (Chemicon International, Temecula, Calif., USA)] evidence the presence of several plaques in both the paracingular cortex and neostriatum (FIGS. 9A and 9B).

Figure 12:
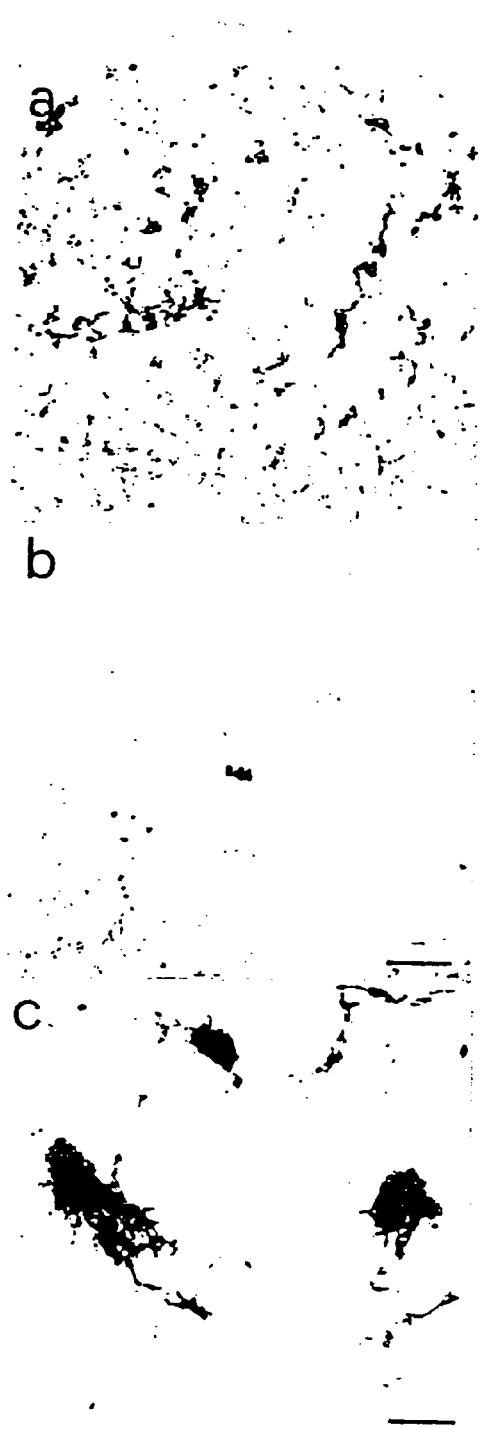
FIG. 12 Amyloid deposits in the cortex of aced anti-NGF transgenic mice. Anti-APP immunoreactivity in cortical sections from anti-NGF (a) and control mice (b). The numerous extracellular amyloid deposits found in the cortex of anti-NGF transgenic mice show, at high magnification (c), a fibrillary nature. Scale bar in a, b=75 µm; c=25 µm.

The experiments were carried out using both immunohistochemical and Western blot techniques (see above). The results showed that, 15 months after birth, amyloid plaques are present in both the cerebral cortex and hippocampus of anti-NGF mice (FIG. 12). These plaques cover a significant part of the enthorinal cortex surface, the percentage values being 21% of the surface compared to 0.5% in control mice. In other regions of the cerebral cortex the percentage of the surface covered by amyloid plaques is 10% and 0.1% in the anti-NGF mice and control mice respectively. The values are 4% and 0.1% in the hippocampus of the anti-NGF and control mice, respectively.

Figure 13:
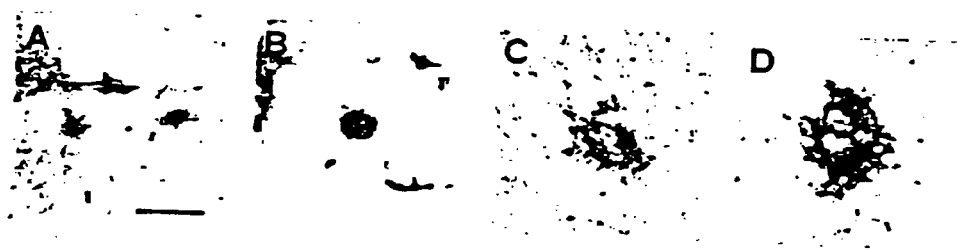
FIG. 13 Presence of compact amyloid Plaques Compact amyloid plaques are observed in the subcortical white matter (A) and cerebral cortex (B) of 6 months-old anti-NGF mice. In 15 months-old anti-NGF mice plaques assume a fibrillary appearance with irregular contours (C) similar to that observed for typical plaques in AD human brains (D). Scale bars in A 150 µm; in B–D=75 µm.

The plaque distribution and their morphology in the anti-NGF mice are entirely comparable to those observed in sections of patients affected by Alzheimer's disease (FIG. 13). From above data it can be concluded that the anti-NGF mice display a high extracellular deposition of amyloid as plaque aggregates similar, as for morphology and distribution, to those observed in human brain sections of patients affected by Alzheimer's disease.

Figure 14:
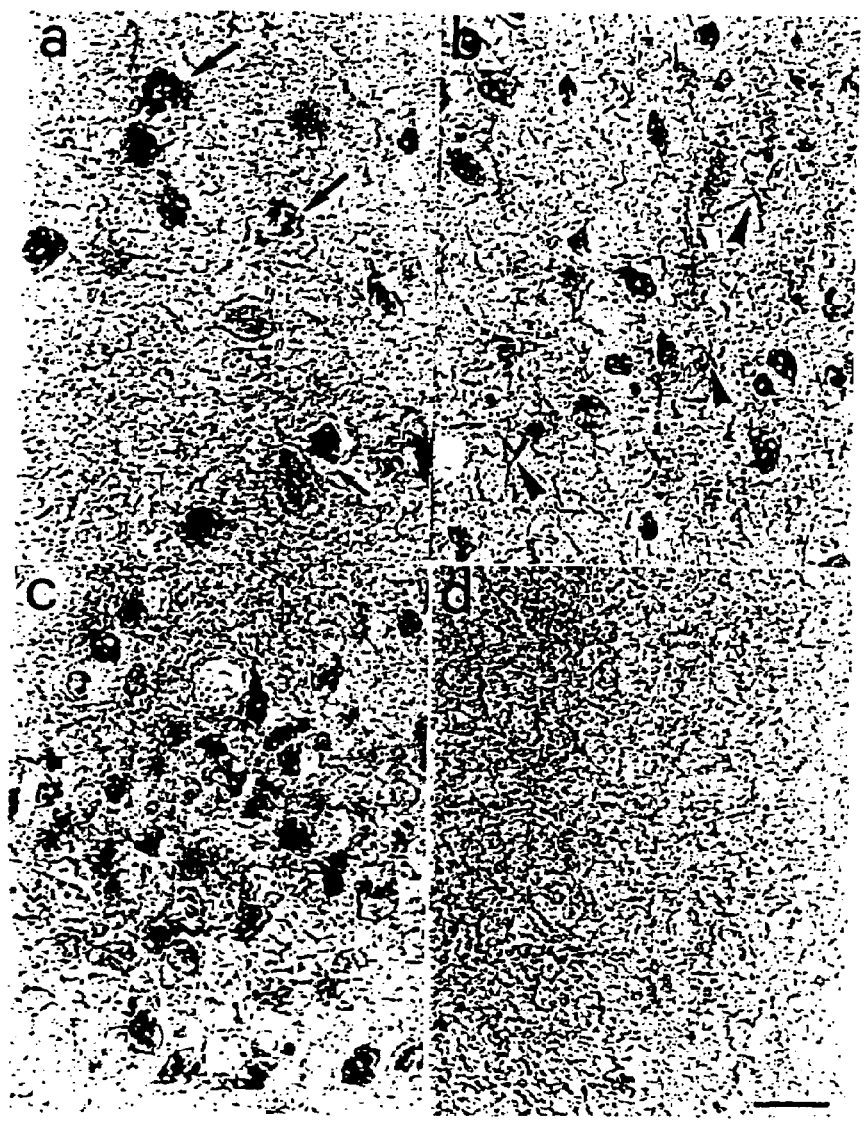
FIG. 14. Immunostaining with the anti-tangle antibody mAb NFT200. a, b, c Sections through the parietal cortex (a, b) and the entorhinal cortex (c) of anti-NGF transgenic mice. The NFT200 antibody reveals the presence of tangles in pyramidal cells (arrows) and of dystrophic neurites (arrowheads) d, No labelling is seen in sections from transgenic control mice. Scale bar=25 µm.
Figure 15:
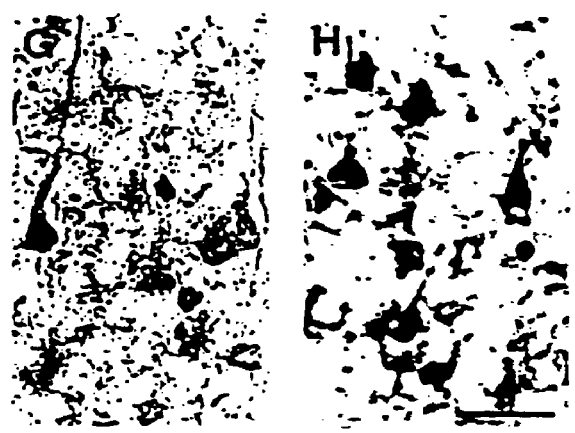
FIG. 15. Neuron labelling by anti-NTF200 anti-tangles antibodies Anti-tangles NFT200 antibodies label neurons both in aged anti-NGF mice (G) and in AD human cortex (H). Scale bars 50 µm.

(f) Presence of neurofibrillary tangles in neurons of anti-NGF mice. The presence of intracellular tangles in brain sections of anti-NGF mice was showed using mAB NFT200, an antibody recognizing neurofibrillary tangles in AD brains (Innogenetics, Gand, BE). mAB NFT200 labelled many neurons distributed throughout the brain of anti-NGF mice (FIGS. 14a–c), but not in control animals (FIG. 14d). The antibody detected the presence of intracellular inclusions in dystrophic neurites too. In FIG. 15 it is possible to compare the distribution of tangles in anti-NGF mice and in brain sections of Alzheimer patients.

The mAB NFT200 antibody reveals, in the brain of anti-NGF mice, aggregates similar to those observed in sections of human brain. This feature, indispensable to confirm the diagnosis of the Alzheimer disease in humans, was never detected up to now in other animal models partially reproducing this pathology.

Figure 17:
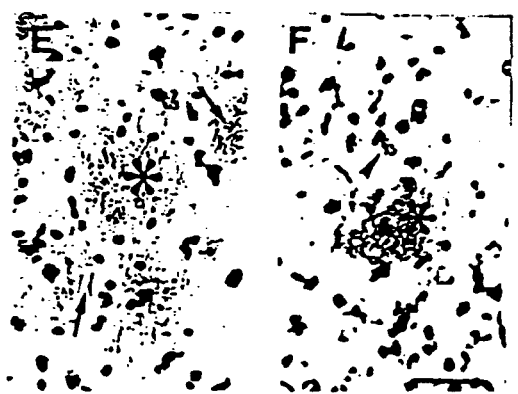

Neurofibrillary tangles were also detected by silver staining. For these experiments a silver staining technique (Bielschowsky method), previously used to detect extracellular neuritic plaques and tangles in brain sections of Alzheimer patients, was used. In anti-NGF-mice this technique allowed to detect the co-existence of dystrophic neurites and extracellular fibrous material in the form of plaques (FIGS. 17E,F). These aggregates are evident in 6 and 15 month old mice.

The silver staining is a histological technique which allowed, independently from immunohistochemical techniques, to detect the presence of plaques consisting of extracellular deposited material and dystrophic neurites. In addition this technique allowed to detect the co-existence of these two modifications. The attempts to detect these modifications in other animal models for the Alzheimer disease has failed so far.

Figure 16:
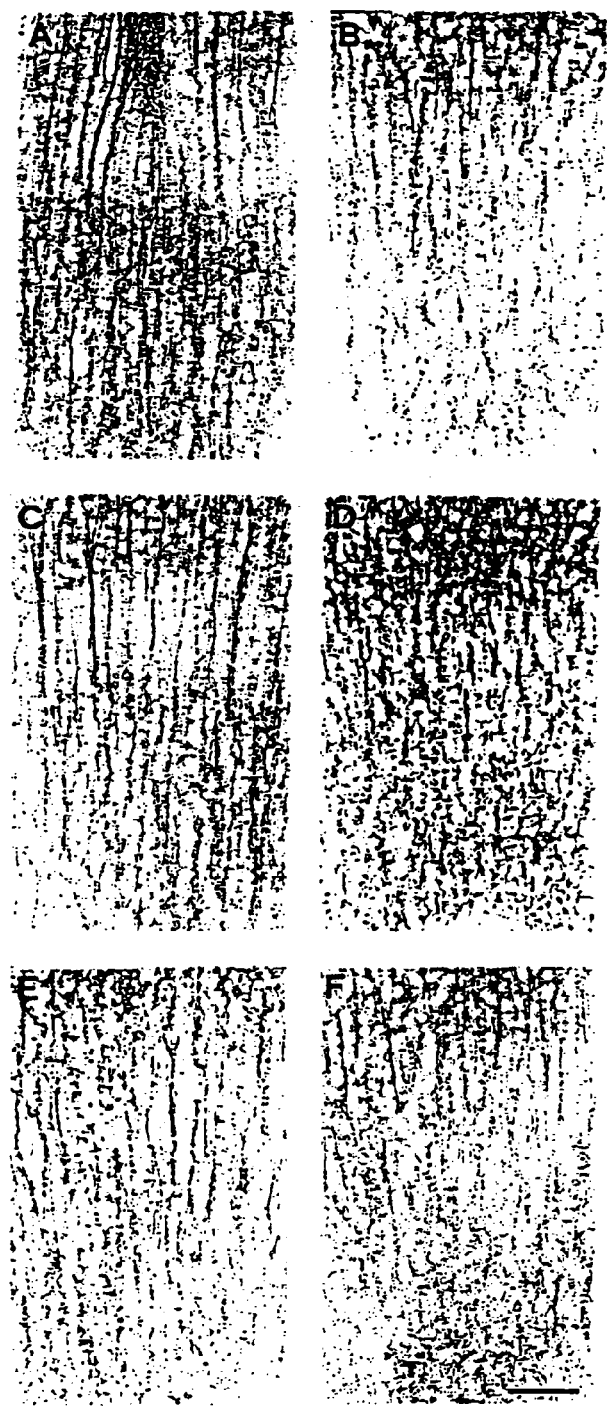
FIG. 16 Time progression of neuron labelling by anti-MAP2 antibodies MAP-2 abnormal distribution in anti-NGF mice. At 2 (A), 6 (C) and 15 (E) months of age anti-MAP-2 (Sigma, St. Louis, Mo., USA) labels the full length of cortical dendrites in control mice. In anti-NGF mice, a reduction of the number of labeled-dendrites and a re-distribution of the staining is observed. The decrease in staining starts at 2 months of age (B) and proceeds with aging (D, F: 6 and 15 months of age, respectively). Scale bar=100 µm.

(g) Modifications of the distribution of MAP-2 (protein associated to microtubules). The protein associated to the microtubules (MAP-2) is part of the multiplicity of the proteins forming the cytoskeleton of neurons. The modifications of said protein were detected using the anti-MAP-2 antibody (Sigma, St Louis Mo.). 1 and 1.5 months after birth the observed distributions of the MAP-2 protein in the cortex neurons of anti-NGF transgenic and control mice were similar. 2 months after birth in the control mice the MAP-2 labelling is distributed throughout the dendrites lengthwise (FIG. 16A). At this age in the anti-NGF mice a decrease in the number of labelled dendrites and a labelling redistribution in the dendrite lengthwise are observed (FIG. 16B). 6 and 15 months after birth the number of dendrites is still decreasing in the anti-NGF mice. In the dendrites of these animals a clear labelling re-distribution is also observed, which is localised in the proximal zone of dendrites (FIGS. 16D,F). In the same age control mice, the MAP-2 labelling is still distributed throughout the dendrites lengthwise (FIGS. 16C,E).

From these results it can be deduced that the NGF deprivation determines a modification in the distribution of the cytoskeleton proteins of the cortical neurons. This modification could be part of the neurodegenerative phenomena leading to the occurrence of the Alzheimer disease.

Figure 18:
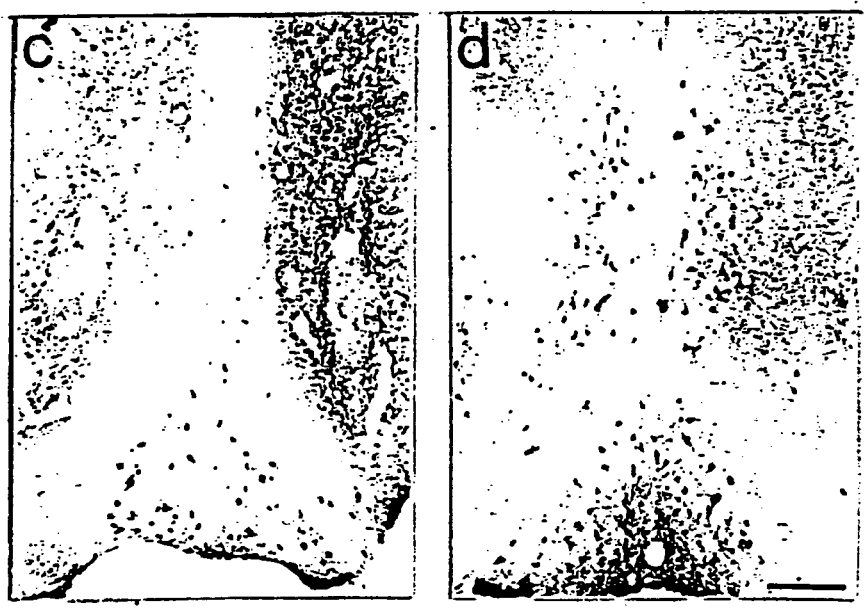
FIG. 18 ChAT staining Staining for choline acetyl-transferase (CHAT) in the basal forebrain of anti-NGF transgenic mice (c) and control mice (d) 15 month old. Scale bar 200 µm.

(h) Time course of the neuropathology in anti-NGF mice. Experiments to evaluate the occurrence of modifications in the different phenotype markers were carried out This time course is summarised below and in Table 3:

1. The decrease of cholin-acetyltransferase(ChAT)-positive neurons, previously described (Ruberti et al., 2000), continues 2 months after birth and reaches a plateau 6 months after birth whereupon a 90% reduction in the number of positive neurons in the medial septum (FIGS. 18C,D) is observed.

Figure 19:
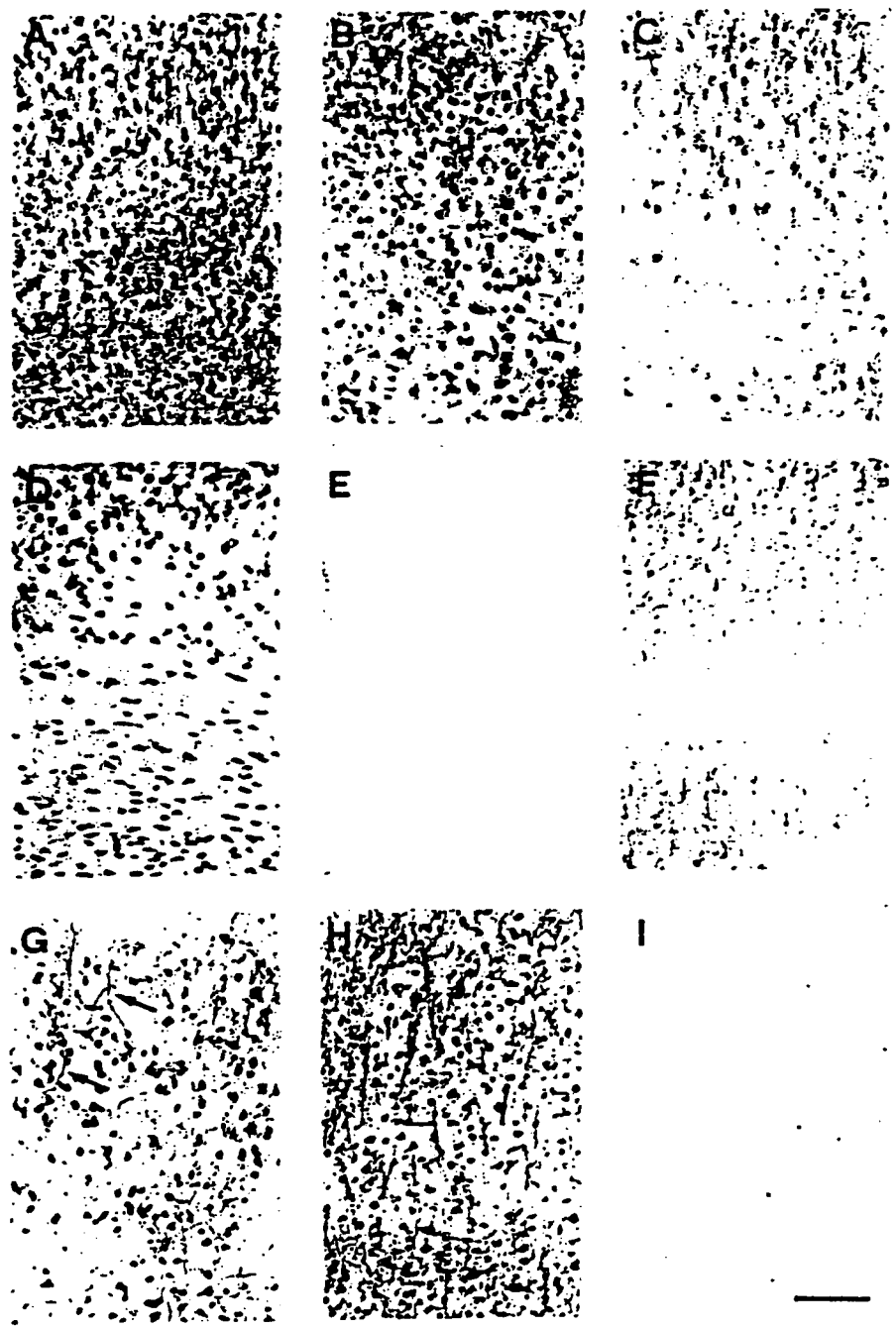
FIG. 19 Tau protein labelling At 1 month of age, AT8 antibodies stain neurons in all cortical layers of the entorhinal (A) and parietal (B) cortices of anti-NGF mice. In both cortices, the labeling decreases at 1.5 months of age (C). No difference is seen with control mice. At 2 months of age, AT8-positive neurons are observed in the entorhinal cortex (D), while only a few cells are faintly labeled in the parietal cortex (F). In age-matched control mice there is no labeling in neuronal bodies (E). In 6 months-old mice most neurons of the entorhinal cortex (G) express AT8 in their cell body and many of them also in dendrites (arrows). At this age, the parietal cortex (H) shows labeling both in neuronal perikarya and dendrites. No labeling (D) was observed neuronal bodies or dendrites of age-matched control mice (I). Scale bar 100 µm.
Figure 20:
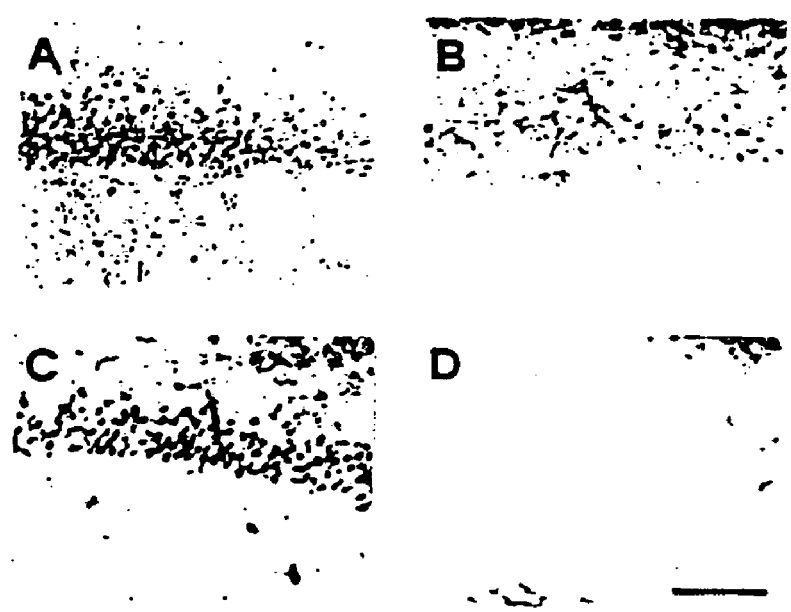
FIG. 20. Tau protein labelling AT270 (A,B) and AT8 (C,D) antibodies labels pyramidal cells in hippocampal CA1 region in 15 month old anti-NGF mice (AT270:A; AT8: C). In age-matched control mice AT270 (B) and AT8 (D) antibodies label only axons. Scale bar 100 µm.
Figure 21:
FIG. 21 Tau protein labelling AT180 (Innogenetics, Gand BE) staining in cerebral cortex of anti-NGF mice increases with age. (E) Cortex of 1 month-old anti-NGF mouse, (F) 6 months-old anti-NGF mouse and (G) 15 months-old anti-NGF mouse. (H) 15 month-old control mouse. Arrowheads point to noneuronal, immunopositive cells. Arrows indicate dystrophic neurites. Scale bar 75 µm.
Figure 22:
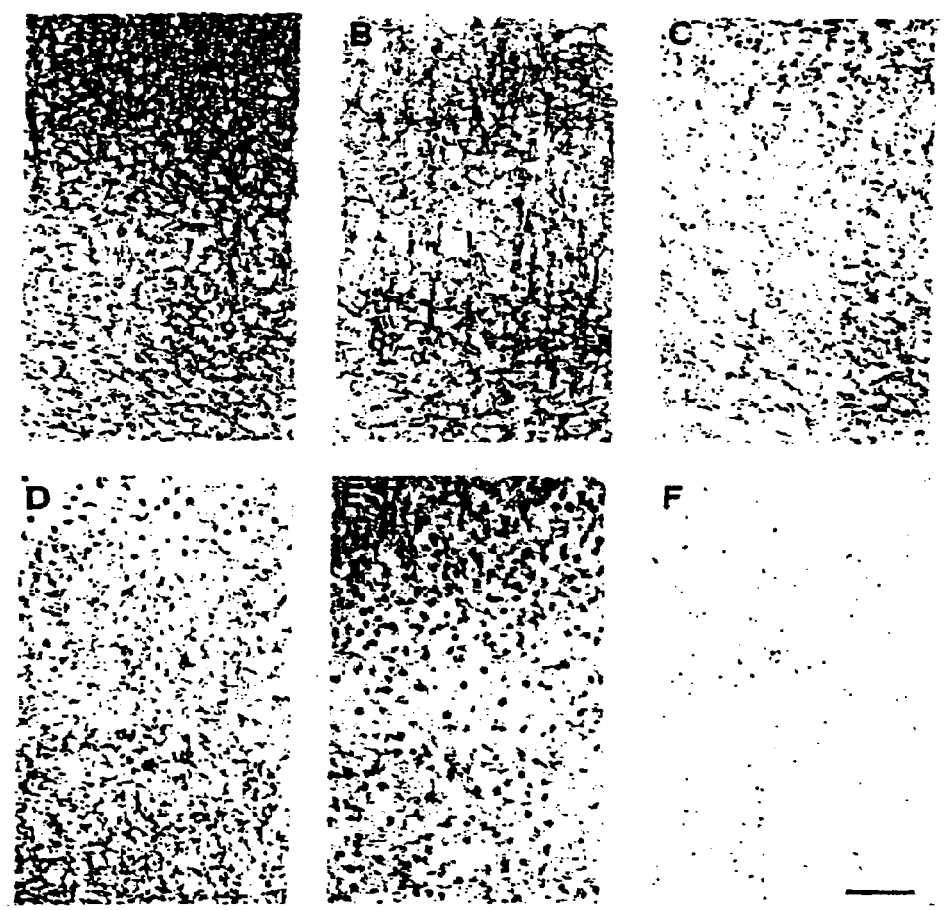
FIG. 22 Tau protein mAb AT270 labelling. AT270 (Innogenetics, Gand, BE) immunolabeling in cerebral cortex of anti-NGF mice at (A) 1 month, (B) 1.5 months and (C) 2 months of age. No difference was observed when compared to control mice. Starting from 6 months of age in anti-NGF mice a specific labeling shows up in neurons of Layer II/III (D). The number of these positive cells increases in 15 months-old anti-NGF mice (E). with respect to control mice (F). At both ages no labeling is observed in age-matched control mice (F). Scale bar 100 µm.

2. The determination of the somatodendritic distribution of the tau protein in hyperphosphorylated form was carried out by different antibodies and, in the anti-NGF mice, showed as follows:

2 months after the birth only the enthorinal cortex presents modification detected by mAB AT8 (FIG. 19), these modifications extend to other regions of the cerebral cortex and hippocampus (FIG. 19 and FIG. 20) from 6 months after birth, these modifications are detected also by other antibodies, different from AT8, i.e. PHF-1, AT180 and AT270 mAbs.

3. The AT8 antibody, used together with extraction techniques, shows that most of the tau protein extracted from the anti-NGF mice brain is insoluble.

4. The cytoskeleton modifications concern not only the protein tau but also MAP-2 protein and start 2 months after birth.

5. The tangle-like inclusions are present only 15 months after birth, whereas the dystrophic neurites are detected already 6 months after birth.

6. The DNA fragmentation is observed only 15 months after birth. In conclusion the anti-NGF mice present a time course of the neurodegeneration starting from the cholinergic deficit and modification of some cytoskeleton proteins. The spatial progress of the pathology is similar to what observed in brain form Alzheimer patients.

TABLE 3

| PHENOTYPIC MARKERS | BRAIN AREAS | Age (months) | | | | |
|---|---|---|---|---|---|---|
| | | 1 | 1.5 | 2 | 6 | 15 |
| ChAT reduction | | — | — | + | ++ | ++ |
| Hyperphosphorylated tau in the somatodendritic compartment | | | | | | |
| AT180 | Entorhinal cortex | — | — | — | + | ++ |
| | Parietal cortex | — | — | — | + | ++ |
| | Occipital cortex | — | — | — | + | ++ |
| | Hippocampus | — | — | — | — | — |
| AT270 | Entorhinal cortex | — | — | — | + | ++ |
| | Parietal cortex | — | — | — | + | ++ |
| | Occipital cortex | — | — | — | + | ++ |
| | Hippocampus | — | — | — | — | + |
| AT8 | Entorhinal cortex | — | — | + | ++ | ++ |
| | Parietal cortex | — | — | — | + | ++ |
| | Occipital cortex | — | — | — | + | ++ |
| | Hippocampus | — | — | — | + | ++ |
| Insoluble Tau | | ND | ND | ND | ND | ++ |
| Abnormal subcellular localization of MAP-2 | | — | — | + | ++ | ++ |
| Neurofibrillary tangles | | — | — | — | — | ++ |
| Amyloid plaques | | — | — | — | + | ++ |
| Inclusions as revealed by silver impregnation | | — | — | — | + | ++ |
| Dystrophic neurites* | Entorhinal cortex | — | — | — | ++ | ++ |
| | Parietal cortex | — | — | — | + | ++ |
| | Occipital cortex | — | — | — | + | ++ |
| | Hippocampus | — | — | — | — | — |
| DNA Fragmentation | Cerebral cortex | — | — | — | — | + |
| | Basal forebrain | — | — | — | — | — |

+ qualitative measure of each phenotypic marker;
ND: not determined;
*as detected by silver and immunohistochemical impregnation by hyper-phosphorylated anti-tau antibodies and <<tangles>>.

The analysis showed that the neurodegenerative pathology at the brain level is preceded by an early (2 months after birth) tau hyperphosphorylation, as detected by the AT8 antibody (which is able to bind to a phosphorylated tau epitope, selectively expressed in Alzheimer affected patients) and amyloid deposition in the back or lower limb skeletal muscles (see in the following). It is to be pointed out that the association of Alzheimer disease with inclusion body myositis in humans is already known.

In summary transgenic mice expressing the anti-NGF antibody resemble at the level of the Central and Peripheral Nervous System many pathological modifications typical in neurodegenerative diseases, particularly Alzheimer disease.

2) Muscular System

Figure 23:
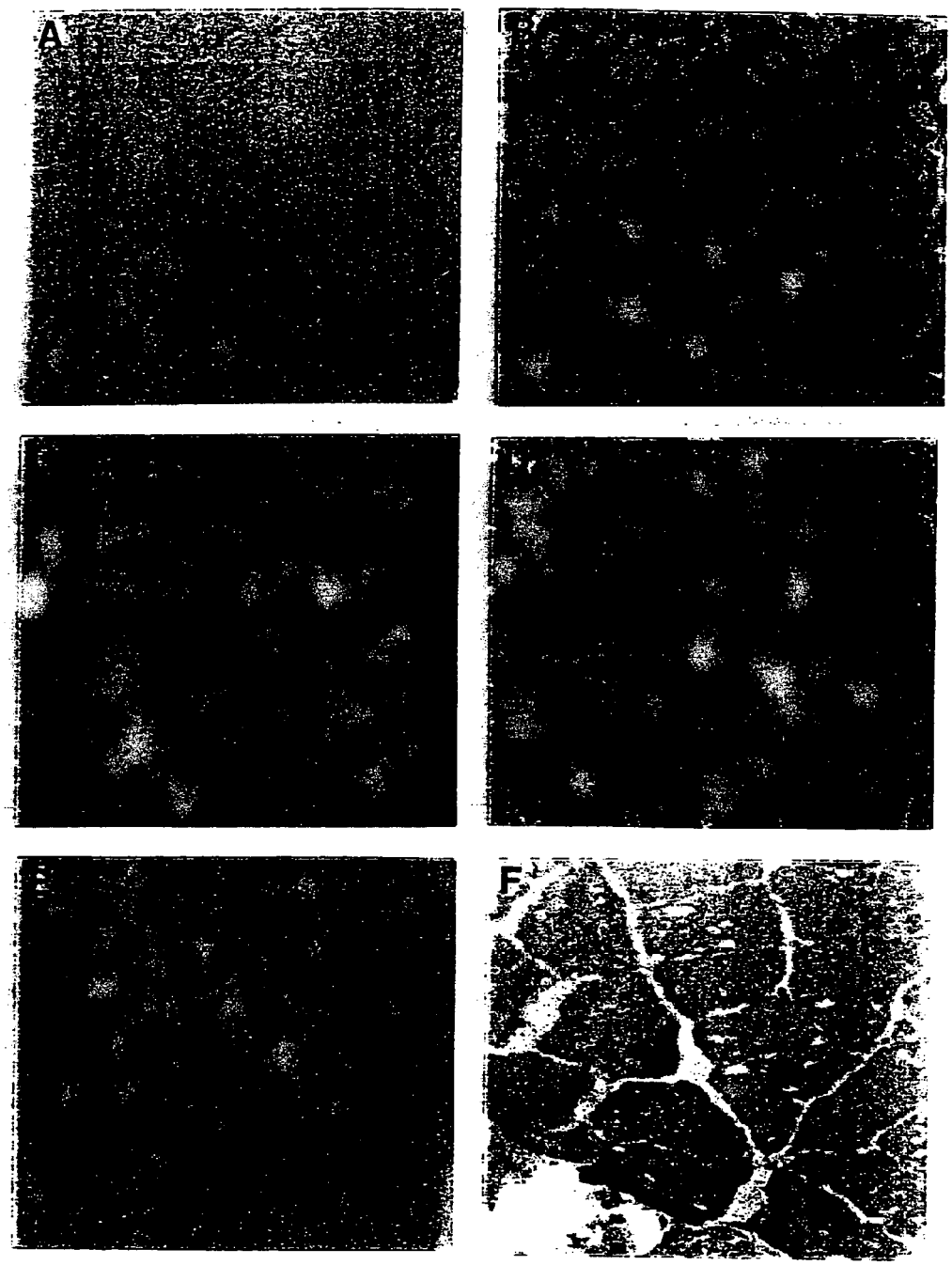
FIG. 23 Muscular atrophy. Transversal sections of skeletal muscles from transgenic mice and anti-NGF mice. Staining: hematoxylin-eosin. M. rectus medialis from the hindlimb of control (A) and Anti-NGF mice (B). M. gastrocnemius from the hindlimb of control (C) and Anti-NGF mice (D). M. tibialis anterioris from the hindlimb of control (E) and Anti-NGF mice (F).
Figure 24:
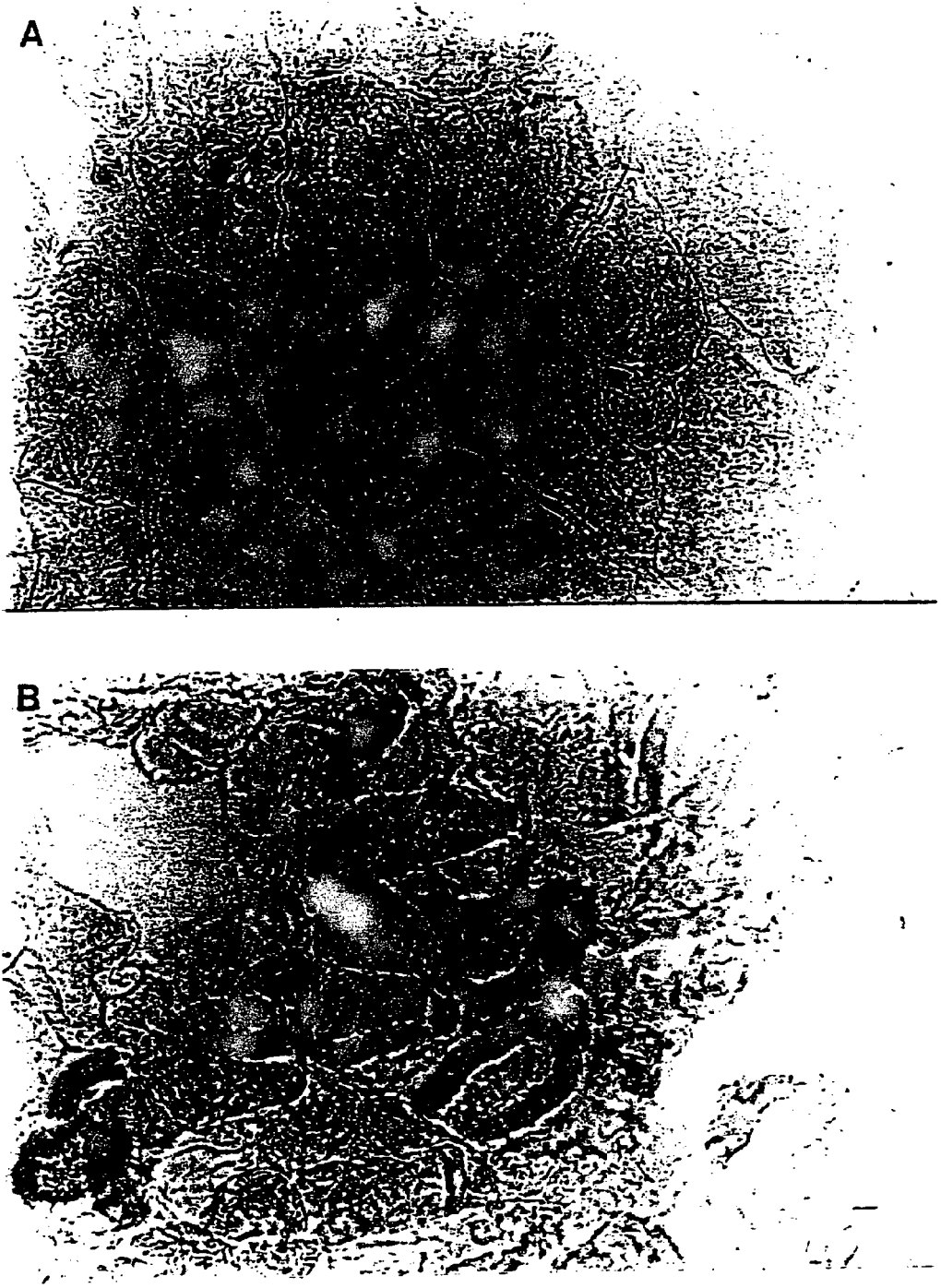
FIG. 24 Amyloid deposition in the muscle. Congo red staining show the presence of amyloid deposition in anti-NGF (B) and control mice (A).
Figure 25:
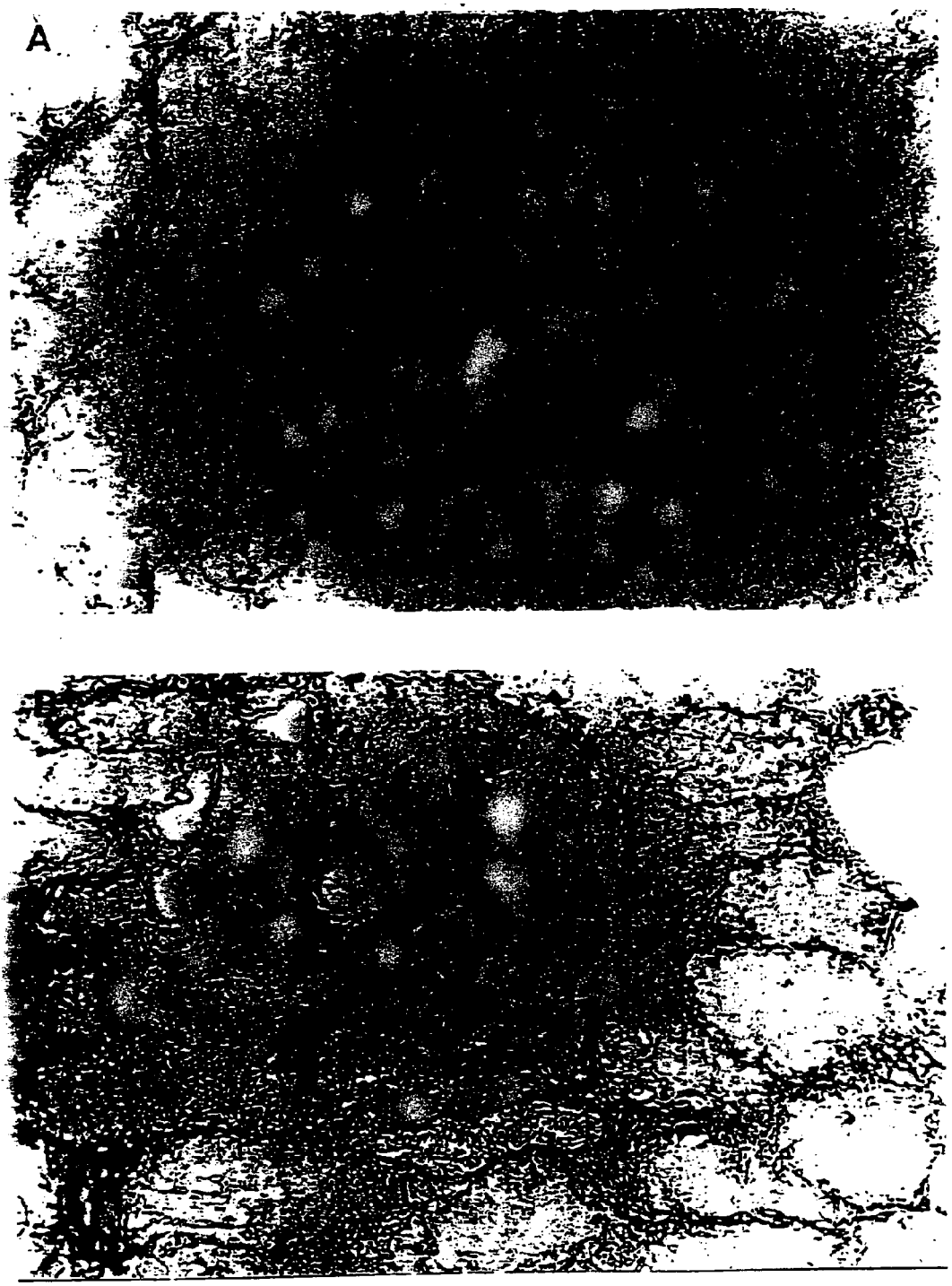
FIG. 25 Amyloid deposition in the muscle The immunoreactivity for amiloyd precursor protein in muscles from aged (15 month old) control mice is completely absent (A). In anti-NGF mice (B) there is an increase of labeling, corresponding to the brown precipitate, in the sarcolemma and cytoplasm of myofibers.
Figure 26:
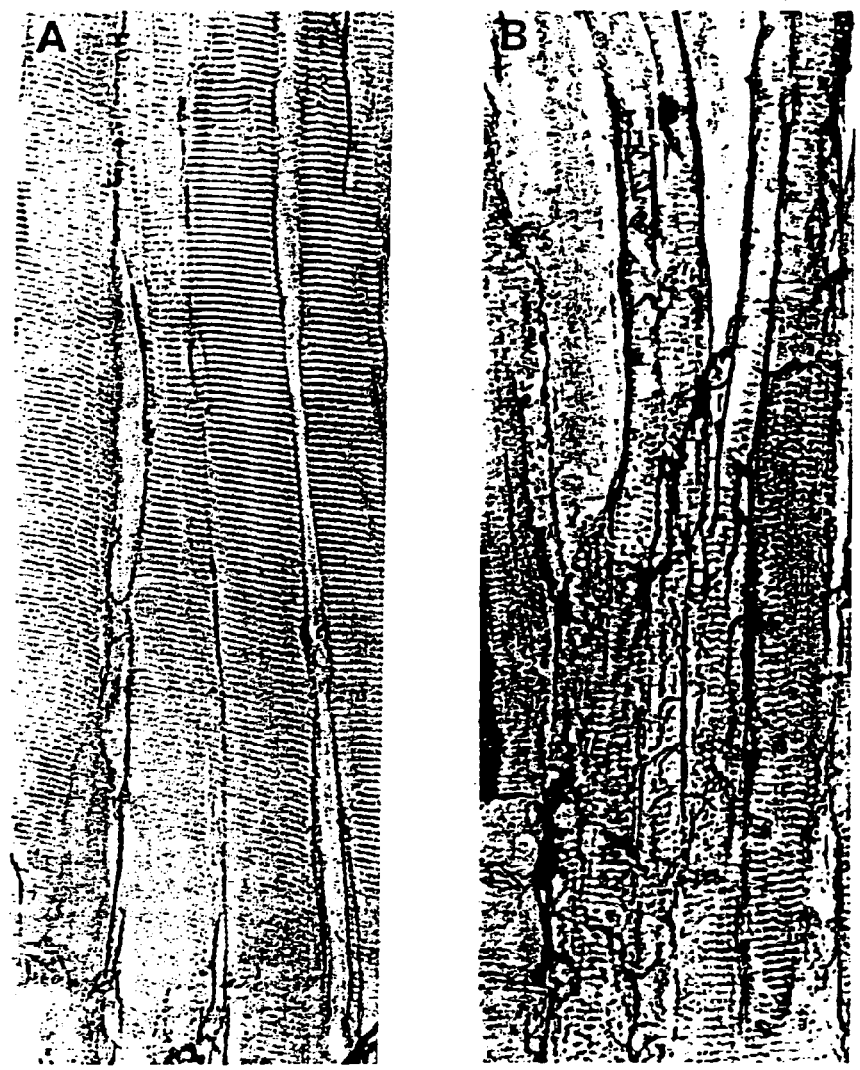
FIG. 26 Phosphorylation of the tau protein in the muscle The immunoreactivity for hyperphosphorylated tau in muscles from aged control mice is completely absent (A). In anti-NGF mice (B) there is an increase of labeling, corresponding to the brown precipitate, in the sarcolemma and cytoplasm of myofibers.
Figure 27:
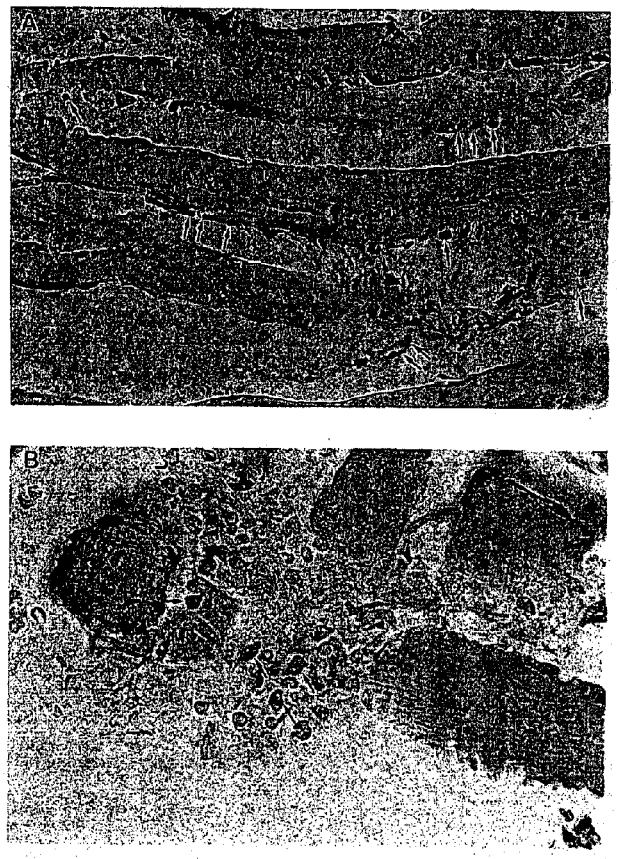
FIG. 27 Macrophage infiltration in the muscle Macrophage infiltration in the muscle. Longitudinal (A) and transversal (B) sections of muscles from aged anti-NGF mice. Immune cells, such as macrophages, are shown between myofibers.
Figure 28:
FIG. 28 Position of the nuclei in the myofibres of the anti-NGF mice In some myofibers from aged anti-NGF mice nuclei are localized at the center of the cell (arrows) and not at the periphery (asterisks).

Mice evaluated (n=15) from 45 to 60 days after birth, at a macroscopic level stagger, due to an abnormal position of the rear legs and support of toe tips and often present backbone scoliosis. The anatomical analysis shows a size reduction of the back longitudinal skeletal muscles, flexor and adductor of the rear limbs, feature not observable in other muscles, for example in the corresponding muscles of the front limbs. Some deficits were better characterised and detailed as follows:

a) muscular dystrophy, characterised from the morphological and histological point of view. The atrophy of the muscular fibres is present, in all the considered animals (n=15), for the muscles which allow the movements of the backbone and aid the stability of the connections of each other vertebra (longest muscle for the backbone and intervertebral muscles, respectively). Further in all the animals the reduction of the diameter of the muscular fibres (up to 50%) is observed in 70% of the fibres: in the adductor (leg medial rectus, large and small adductor), leg flexor (outer, medial and inner ischiotibial) and metatarsus extensor (gastrocnemius and soleus muscles). On the contrary the atrophy is not present at the level of the metatarsus flexor muscles (front tibial and phalanx extensor muscles) and it is less evident in the front limb extensor muscles (brachial triceps muscle). All these differences are showed in FIG. 23. Further every dystrophic muscular fibre show also a remarkable vacuolization (FIGS. 23B–E) and a more intense staining by haematoxylin/eosine.

b) scoliosis, in some animals (n<6), in some cases associated with an incomplete development of the vertebral bodies.

c) muscular atrophy, typified at molecular level as follows:

c.1) re-expression of the low affinity NGF receptor (p75). It is particularly clear in some muscular cells also exhibiting modifications in the distribution of nicotinic receptors at the level of the neuromuscular junctions.

c.2) decrease in the number of nervous peptidergic endings at the level of neuromuscular junctions. This decrease was detected by antibodies against the calcitonin gene-related peptide [CGRP (Gibson et al., 1984)].

c.3) absence of the aggregation of the acetylcholine receptors in the plasmatic membrane of the muscular cells, as detected by the irreversible binding of alfa-bungarotoxin (Changeux, 1991), caused by the reduced innervation of the muscular fibre. The distribution of the muscular cells exhibiting such a modification gives the muscles of the transgenic mice a characteristic mosaic pattern.

c.4) increase of the immunoreactivity for dystrophin, detectable, in the above described cells exhibiting molecular modifications, by immunohistochemistry using D-8043 antibody (Sigma). Dystrophin is a protein of the skeletal muscular cell involved in muscular contraction and in the aggregation of the cholinergic receptors. It is already known that an increase in the dystrophin synthesis occurs concurrently with muscle denervation.

c.5) ATPase decreased metabolism due to the lack of the nerve trophic effect.

c.6) remarkable deposition of amyloid substance, detected by a characteristic ring cytoplasmic staining by Congo Red (FIGS. 24A–B). The presence of amyloid and particularly β-amyloid was detected also by immunohistochemistry against the β-amyloid precursor protein (FIG. 25A–B) in <<aged>> mice.

c.7) phosphorylated tau protein in the muscles of the aged mice (age from 15 to 18 months). FIGS. 26A–B.

c.8) presence of various muscular fibres with nuclei located at the center of the fiber, rather than below the sarcolemma in aged anti-NGF mice (FIG. 28). Histological assays detects an infiltration of immune type cells, probably macrophages, among the muscular fibres (FIGS. 27A–B).

The presence of deposits of the β-amyloid and hyperphosphorylated tau protein and in addition nuclei located in the middle region and macrophages infiltration, is related to what observed in inclusion body myositis (IBM), a pathology strictly correlated with the Alzheimer disease.

3) Spleen

At the anatomical level the localisation of the sympathetic innervation is distributed in the germinal centre and marginal zone, rather than in the proximity of the central artery, as in the control mice. The recovery of the viable splenocytes is reduced by one order of magnitude ($2-3\times10^6$ vs. $2-3\times10^7$ of the controls) in the anti-NGF transgenic mice, as observed by flow cytometry. Functionally a reduction of the number of the IgG positive lymphocytes can be observed and a fair increase of the IgD positive lymphocytes, as measured after incubation (30', 4° C.) of the splenocytes with FITC anti-IgG (Sigma), IgM, IgA, IgD mouse (Pharmingen) labelled primary antibodies and analysis by Coulter Epics Elite Esp Flow Cytometer at 488 nm. Furthermore in the red pulp DNA fragmentation, indicating apoptosis, can be detected, consistently with the reduced recovery of viable splenocytes.

EXAMPLE 3

Analysis of the Behaviour of Anti-NGF Transgenic Mice

Figure 29:
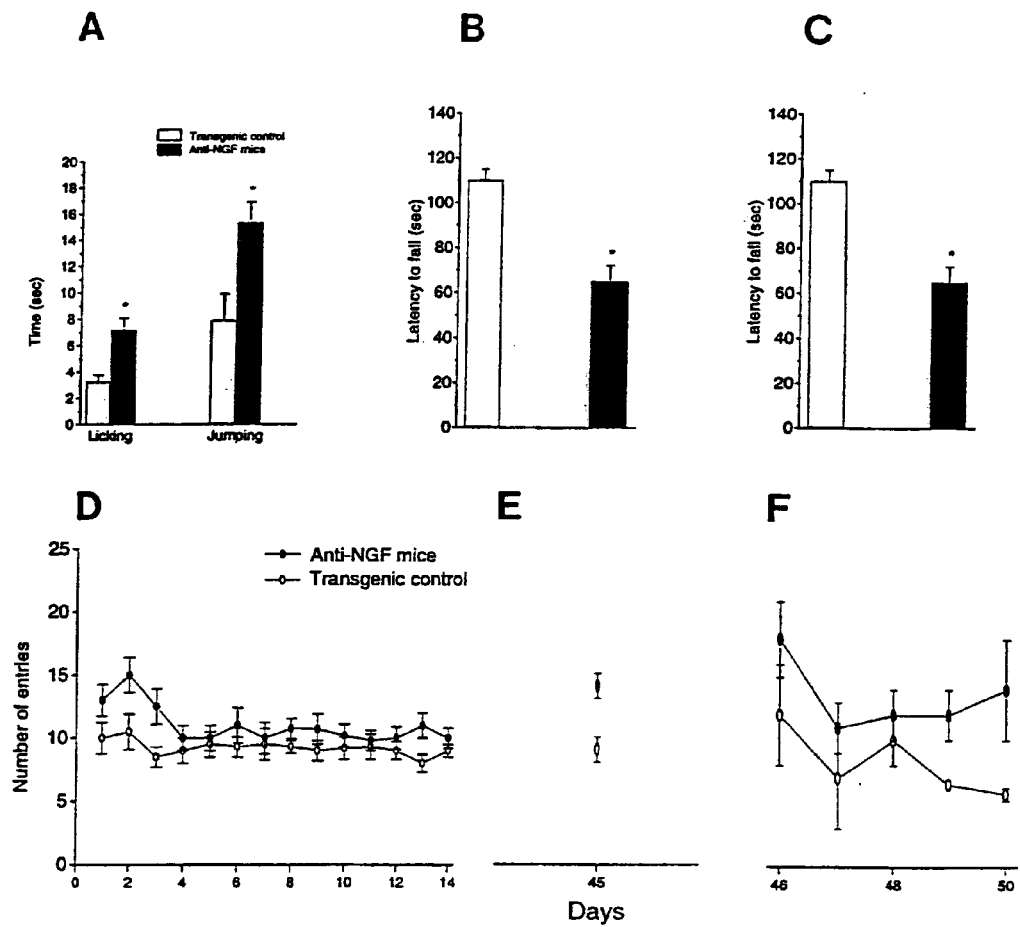
FIG. 29 Behavioral analysis of anti-NGF transgenic mice. (A) Nociceptive test in anti-NGF transgenic and transgenic control mice. Values are the mean±SEM, n=10 for each group of animals (B) Open field test. (C) Rotarod test. *, P<0.05. (D) Spatial learning curves for anti-NGF transgenic (n=10, filled circles) and control mice (n=10, open circles) mice in a radial 8 arms maze (four arms baited). Vertical bars are the standard errors. The number of arms entries necessary to find all four food pellets is reported as a function of time. (E) Retention test, 31 days after the end of the learning test. (F) Transfer test, started the day after the retention test FIG. 30 Object recognition test The test reveals impairment in discrimination tasks. *, P<0.03.

The analysis was carried out on 12–18 month old animals (n=6), selecting animals without evident gait anomalies. The following anomalies, resumed in FIG. 29, with respect to the control animals were detected:

Increase of the latency time for the heat sensitivity, changed from 3>> for the control mice to 16>> for the anti-NGF mice, as measured according to the hot plate nociceptive assay, already described in Eddy et al., 1953.

Spatial orientation. This was measured by the radial labyrinth test, carried out as follows: the animals were located in 8 arm radial labyrinth and free to feed themselves for 5' and familiarise with the labyrinth over two days. For the test the same four arms were filled with food every day; at the beginning of each test the mice were left at the centre of the labyrinth, free to explore it: the test was terminate if the food was finished or 25 entries were observed into the arms of the labyrinth: the tests were repeated twice a day over 14 days, made mistakes (short and long term memory mistakes) and taken times being measured. The starting and final learning levels were evaluated using the average of the mistakes made over the first and last three days. The anti-NGF mice exhibit a higher number of errors during the working memory learning over the first three days, in fact the learning plots are significantly different (two way RMANOVA test, $p<0.05$), however the final learning level is not different from that of the control mice.

Ability in maintaining the acquired notions. The anti-NGF mice do not maintain the acquired notions at $31^{st}$ day after the final learning step, as measured by the same radial labyrinth test. The learning plots were compared with the two way ANOVA test (treatment× time) and the significance of the differences evaluated by T-test.

Deficit in the ability of learning transfer into other situation, as measured by the radial labyrinth test, using food filled arms, different from those used in the learning step. The anti-NGF mice exhibit a clear learning deficit ($p<0.01$ in two way RMANOVA test) in comparison to the control mice, also after 5 learning days. The differences resulted mainly from a higher number of short term memory errors (T-test, p<0.006).

Figure 30:
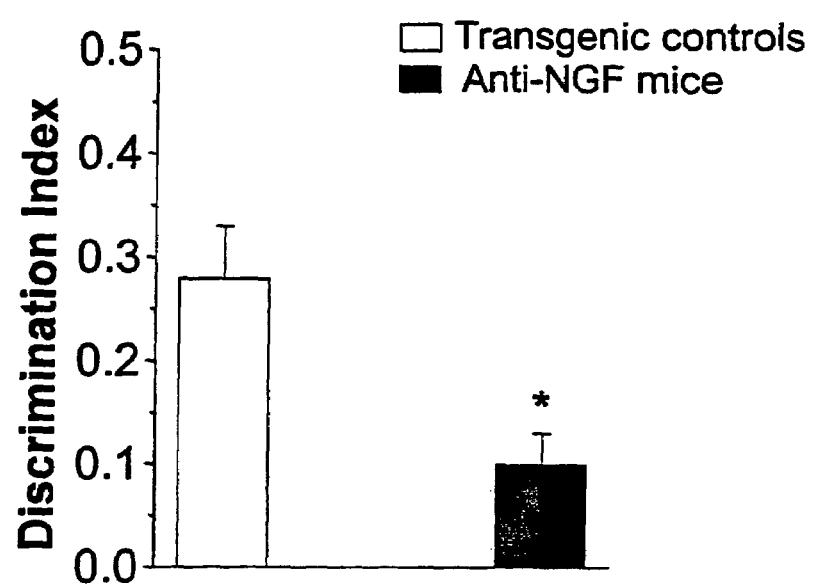

Short term memory test (object discrimination test). According to this test the mice explored 2 white cubes over 10 minutes. Then one cube was coated with white and black chess painted paper. One hour after the end of the first trial the mice were allowed to come again in contact with the cubes and explore them over additional 10 minutes. The anti-NGF transgenic mice were not able to distinguish between the two cubes coated with differently coloured papers (FIG. 30). Therefore the anti-NGF mice show a decrease in the short term memory, not being able to memorise and distinguish between the two differently coloured cubes.

EXAMPLE 4

Reversibility of the Muscular Dystrophy in Anti-NGF Mice by NGF Local Administration All the experiments were carried out on 45 day old mice, when the serum level of the anti-NGF antibody is still not at the highest level (observed 60 days after the birth). The NGF was administered locally by different methods: (a) by intramuscular injection of NGF, (b) by intramuscular injection of a viral recombinant vector (adenovirus) encoding for NGF cDNA or (c) by the implant of NGF secreting fibroblasts. All the administration routes included the injection or implant in the gastrocnemius muscle, one of the skeletal muscles affected by muscular dystrophy. The injections and implants were carried out on the right leg, while the gastrocnemius muscle of the left leg was used as control. A) NGF was injected as pellet, consisting of diazocellulose mixed NGF in borate buffer at pH 8.0 for 72 hours and following neutralisation by glycine saturated solution (Hendry, 1982). This method allows the exact localisation and slow release of this neurotrophin. Different NGF concentrations were used, comprised in the range from 100 μm and 2 mg for each animal. For the administration of cDNA according to the method b), 10 μl of the adenoviral vector solution corresponding to $10^t$ pfu/ml were injected in the gastrocnemius muscle. In the control animals a recombinant adenovirus containing *Escherichia coli* Lac Z reporter gene was injected. Both in this and in fibroblast injection experiment (see later) NGF production was constant at least over one month, allowing the reversibility of the phenotype to be observed.

According to method c) fibroblasts genetically modified to secrete NGF by infection with a retroviral vector encoding for cDNA of this neurotrophin, according to the method described by Gage et al. (1990), were implanted in the muscle. This allowed to obtain an in situ NGF production equal to 100 ng/$10^6$ cells/day. The fibroblasts were injected after re-suspension in sterile physiological saline at a $2\times10^5$ cells/LI concentration. The injection volume was 10 μl/animal.

To verify the effect of the NGF administration the animals were sacrificed 7, 15 and 30 days after the injection. The injected and contralateral muscles were collected and analysed by histological and immunohistochemical techniques to verify the attenuation of the dystrophy and the restoration of usual innervation. Thus it was verified that in all the injected animals the values of the muscular fibre diameter were again similar to those of the control animals. Furthermore their morphology and cholinergic and peptidergic innervation re-assumed an usual appearance.

EXAMPLE 5

Restoration of the CNS Phenotype in Anti-NGF Mice by NGF Local Administration

The restoration of the cholinergic phenotype in the basal forebrain was achieved by two different approaches. In a first set of experiments, NGF was delivered using slow releasing minipumps (Alzet, USA) A rubber capillary tube was inserted in the lateral ventricle and then connected by means of an osmotic minipump to a <<pocket>> of the subcutaneous layer. This pump was filled by NGF (30–100 μg) diluted with Ringer-Locke physiological saline. Experiments were performed in 2 months-old transgenic mice and controls.

In another set of experiments, animals of the same age of previous ones were treated by an implant of fibroblasts genetically modified to secrete NGF. The fibroblasts were injected in the lateral ventricle at a $2\times10^5$ cells/μl concentration. The injection volume was 1.5 μl/animal. This second method allowed to verify, by ELISA, the constancy of NGF production over 4 weeks after the implantation. The analysis of the cholineacetyl transferase expression (ChAT) in the nuclei of the basal forebrain and the analysis of the behaviour of these mice allowed the phenotype reversibility to be observed in the anti-NGF mice at the level of the cholinergic system.

As a whole these results confirm that the NGF administration is able to correct the muscular and cholinergic deficit observed in the anti-NGF mice.

EXAMPLE 6

Rescue of the Cholinergic Phenotype in Anti-NGF Mice

Since at 2 months of age cholinergic deficit is one of the first signs of neurodegeneration, the authors evaluated the possibility of restoring the cholinergic neuronal loss using two different approaches. The first one is based on the systematic injection of L-thyroxine (LT4), an hormone that is known to produce an increase of NGF synthesis and a consequent increase of ChAT in neurons of the basal forebrain (Luesse et al., 1998). In a second series of experiment a phage library was used to identify a peptide that has a sequence different from NGF and could compete for the binding site of the monoclonal antibody αD11. Th phage carrying the selected peptide was intraventricularly injected in anti-NGF mice brain. The aim of these treatments was to increase the availability of free NGF to target cells. The effects of LT4 and the synthetic peptide were analyzed both at the level of cholinergic neurons of the basal forebrain and of NGF synthesis in brain, submandibular glands and blood serum.

Materials and Methods

Animals. Control (VH only) mice and anti-NGF transgenic mice were generated following the injection of DNA fragments containing the transcriptional units of the light and heavy chain of chimeric αD11 antibody, placed under transcriptional control of the ubiquitous human cytomegalovirus early region promoter (Ruberti et al., 2000). Mouse genotype was verified by PCR analysis of tail DNA Animals were maintained on a 12-h light, 12-h dark cycle and fed ad libitum. All experiments were performed following European Community rules for animal care.

Phage-display peptide technology. To display large collections of peptides on the surface of phage, mixtures of oligonucleotides containing regions of randomized sequence have been inserted into the N-terminus of the product gene encoding pVIII protein. A seven amino acid random peptide library exposed on the major coat protein VIII with a diversity of 2.2 107, kindly provided by G. Cesareni, was used in these experiments.

Biopanning. Polystyrene beads were incubated overnight at 4° C. with 1 μg/ml of αD11 in 0.5 M carbonate buffer pH 9.6. After washing with PBS and $H_2O_2$, the beads were blocked by incubating with TBST (50 mM Tris/HCl pH 7.5, 150 mM NaCl, 0.5% Tween 20) and 10 mg/ml bovine serum albumine (BSA) for 4 hrs at 4° C. and washed briefly in TBST.

One bead was then added to 1 ml of TBST containing 1 mg/ml BSA, 2.5 $10^{10}$ pfu/ml of UV-killed (defective in replication) phage particles (M13) and incubated with rotation at 4° C. for at least 4 hrs. Then, the pVIII phage library was added ($210^9$ pfu/ml) and incubated overnight at 4° C. Supernatants were collected and stored. After washing in TBST the bead was transferred into a glass tube containing 1 ml elution buffer (0.1N HCl pH 2.2, 1 mg/ml BSA) and incubated under strong agitation at 37° C. for 10 min. The eluted phages were transferred to a polypropylene tube and neutralized by adding 100 □l of 2 M Tris/HCl pH 9.00. As a final step, supernatants and adsorbed phages were titred. A maximum of 3 rounds of biopanning was performed.

Phage amplification. The eluted phage particles were plated onto a bacterial layer overnight at 37° C. The next day, phage plaques were scraped by adding 5 ml of (LB). The obtained suspension was shaked at 37° C. for 30 min, spun at 4,000 r.p.m. for 15 min. The phage particles were precipitated by adding 1/5 volume of PEG NaCl (20% polyethylene glycol 6000, 2.5 M NaCl) to the supernatant, mixed and left stand for 1 h at 4° C. After spinning at 11,000 rpm for 30 min, the pellet was resuspended in 1 ml of water, transferred into a 1.5 ml eppendorf tube, kept for 10 min at 70° C., spun for 5 min in microcentrifuge. The supernatant was transferred to a new tube, PEG/NaCl was added, mixed and left stand for 20 min at 4° C. After spinning, the supernatant was discarded and the pellet was resuspended in 1.5 ml of water, centrifuged for 2 min, filtered through a 0.45 μm sterile filter and titred.

Plaque immuno-screening. Adsorbed phage particles were plated on LB and incubated for 3 h at 37° C., then a nitrocellulose filter was overlaid on the plate and left overnight at 37° C. and then for 1 h at 4° C. Filters were washed 4 times in 5% non-fat dry milk/PBS for 30 min at room temperature under agitation. The filters were then incubated with αD11 (1 μg/ml in 5% milk/PBS) overnight at 4° C., washed in 0.1% Tween/PBS at 4° C. The reaction was revealed using an alkaline phosphatase conjugated antimouse antibody (Sigma), for 4 hours at 4° C., followed by incubation in NBT and BCIP.

Rapid Sequencing of ssDNA phages. The plaques that showed a strong and positive reaction on nitrocellulose filter were sequenced. SsDNA templates were prepared as described and resuspended in 10 μl of $H_2O_2$. R156 (5' AACCATATATTCGGTCGCTGAGGC3') [SEQ ID NO: 1] has been used as primer oligonucleotide for phage sequencing.

Single ssDNA template were subdivided in 4 wells of a 96-well plate, incubated with 2 μl of annealing mixture (6 μl $H_2O_2$, 2 μl sequenase reaction buffer 5×, and 1 pM primer oligonucleotide) at 55° C. for 15 min. Then, 2 μl of reaction mixture (7 μl $H_2O_2$, 0.5 μl $^{35}$S-ATP, 0.4 μl 0.1M DTT, 0.4 μl labelling mix, 0.25 μl USB Sequenase 5.0) were added to each well. Sequencing was performed using sequenase USB kit, according to the manufacturer instructions.

Phage ELISA assay. Ninety-six well plates were coated with 100 μl of rat anti-pill monoclonal antibody (57D1, gift by P. Delmastro) diluted in coating buffer (1 μg/ml 50 mM carbonate buffer pH 9.6) and incubated overnight at 4° C. Palts were washed in PBST and blocked in 5% milk/PBST for 1 h at 37° C. on a rocking platform. After 1 brief wash, a mixture of cleared phage supernatant (50 μl) and 50 μl of 5% milk/PBST was added and incubated for 1 h at 37° C. The plates were washed and 100 μl of αD11 antibody dilution (1 μg/ml in 5% milk/PBS) were added and left overnight at 4° C. After washing, an alkaline phosphatase conjugated anti-mouse antibody was added and left at 4° C. for 4 hrs. The reaction was developed by adding 200 μl of the substrate solution (10% dietanolamine, 5 mM $MgCl_2$ pH 9.6) for 2 min followed by an incubation at 37° C. for 1 h in 100 μl of developing solution (1 mg/ml NTB in 10% dietanolamine, 5 mM $MgCl_2$, pH 9.6).

Peptide 18 treatment. Prior to the injections, phages carrying the peptide 18 or a peptide raised against NT-3 (negative control) were amplified by infecting 2.5 ml of an overnight colture of DH5alpha F' bacteria with 5 ml of phage supernatant in 1 liter of 2TY. After an overnight incubation at 30° C., bacteria were removed by centrifugation at 6000 rpm for 20 min at 4° C. Phage particles were precipitated by adding 1 volume of PEG/NaCl (20% PEG6000, 2.5 M NaCl) to 5 volumes of the supernatant. After mixing, the solution was left stand overnight at 4° C. and spinned at 600 rpm for 30 min. The pellet was resuspended in 40 ml of $H_2O_2$, kept at 65° C. and then spun for 5 min at 11000 rpm.

One volume of PEG/NaCl was mixed to 5 volumes of the phage containing supernatant and incubated for 2 hrs at 4° C. After spinning at 11000 rpm for 5 min., the pellet was resuspended in PBS, spun again to remove cell debris and filtered through a 0.22 μm sterile filter. The phage suspension was then titred by infecting 100 μl of an overnight colture of DH5α F', mixed with LB top agar and plated on LB plates. Phages carrying the carrying the peptide 18 or a peptide binder of anti-NT-3 ($10^9$–$10^{12}$ pfu/μl) were injected in both lateral ventricles. Phages were injected at postnatal day 53 (P53) and mice were killed 1 week after the injection. For the injection, mice were anaesthetised with 2,2,2-Tribromoethanol (0.2 ml/10 g body weight of a 1.2% solution). One μl of phage suspension was injected using a 17 gauge needle connected to a 10 μl Hamilton by a polyethylene cannula, 1 mm lateral and 1 mm anterior to Bregma. After the injection, animals were treated with ampicillin (1 mg/kg) every day, in order to prevent any bacterial infection. Experiment were performed three times for a total number of animals equal to 14 for each group of treatment.

Phage detection. Levels of phage were analyzed in the brain of each animal using brain slices containing the basal forebrain. Samples were sonicated twice for 10 sec. in 200 μl of PBS. Fifty μl were used for direct titration. One hundred and fifty μl were used to infect a colture of DH5αF' to amplify phage particles and after an overnight incubation at 30° C., phages were precipitated and titred.

L-thyroxine treatment. L-T4 was administered according to schedule and dosages which were shown previously to produce the maximal effects, at least within submandibular gland of normal mice (Raynaud, 1964). L-T4 was administered intraperitoneally (10 μg in 0.1 ml of 0.1 mM sodium carbonate in phosphate buffered saline (PBS)) daily from P45 to P62 (n=16). Anti-NGF mice injected with vehicle (n=15) were killed at the same time as the experimental animals.

Immunohistochemistry. Transgenic controls and anti-NGF mice were anaesthetized with 10.5% chloral hydrate/saline (8 μl/g body weight), and transcardially perfused with ice-cold PBS. Brains were removed, fixed in 4% paraformaldehyde/PBS for two days at 4° C. and cryoprotected in 30% sucrose overnight. Coronal sections (40 μm thick) were collected in 1% paraformaldehyde/PBS, preincubated in 10% fetal calf serum and processed for detection of different antigens using avidin-biotin horseradish peroxidase Elite Standard kits (Vector laboratories, Burlingame, Calif.). The following primary antibodies were used: anti-choline acetyl transferase (ChAT; Chemicon, Temecula, Calif., 1:500) and the monoclonal antibody against phosphorylated tau (AT8; Innogenetics, Gand, Belgium). Parallel sections from transgenic and age-matched transgenic control (VH only) mice were processed at the same time.

Quantitative stereology. The volume of basal forebrain and the number of BFCNs was evaluated in 9 anti-NGF transgenic mice and 8 transgenic controls by using a stereological approach (Ruberti, 2000).

Determination of free NGF. The levels of free NGF (i.e. NGF not bound to the transgenic antibodies) in the different tissues was determined by an ELISA assay. This assay exploits the property of αD11 antibody to recognize NGF in a two-site ELISA format 16. Samples of blood serum or of tissue extracts (derived as in Molnar et al., 1998) were added to wells coated with mAb αD11 (coating concentration of 5 mg/ml). After incubation for 2 hours at r.t. and extensive washing with PBS-0.05% Tween 20, followed by PBS, free NGF, not engaged with transgenic αD11, was detected using an affinity-purified rabbit anti-NGF polyclonal antiserum.

Results

Screening of phage display libraries. The data obtained by the successive rounds of biopanning showed that a positive selection was occurring (data not shown). After plating and the formation of individual plaques, the immunoscreening procedure allowed to select only those peptides that bind the antibody in the same region as NGF. The □D11 antibody showed 70% of positive clones in filter immunoassay.

Figure 31:
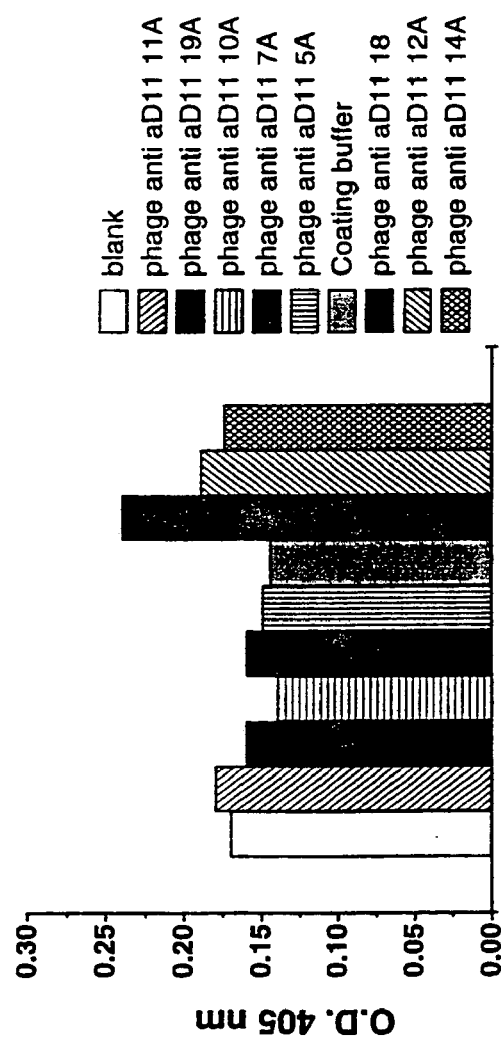
FIG. 31 Phage ELISA The data show that the stronger binder is the phage engineered to carry the peptide 18.

Positive phage clones were analyzed by the single strand DNA sequencing. The positive phage clones were sequenced and re-tested using dot blot experiments towards the αD11 antibody. At least twenty were analyzed. A group of phages selected against αD11 was tested by ELISA to identify the phage clone with a stronger binding activity (FIG. 31) that resulted to peptide 18, having the following sequence RGSRHDL (SEQ. ID. NO: 2). An immunoscreening in which the binding of the antibody to phage was competed by NGF was performed and demonstrated that selected peptides could compete with NGF for the binding to the antibody.

A parallel selection was performed with anti-NT-3 antibodies to exclude the binding to non relevant antibodies.

Figure 32:
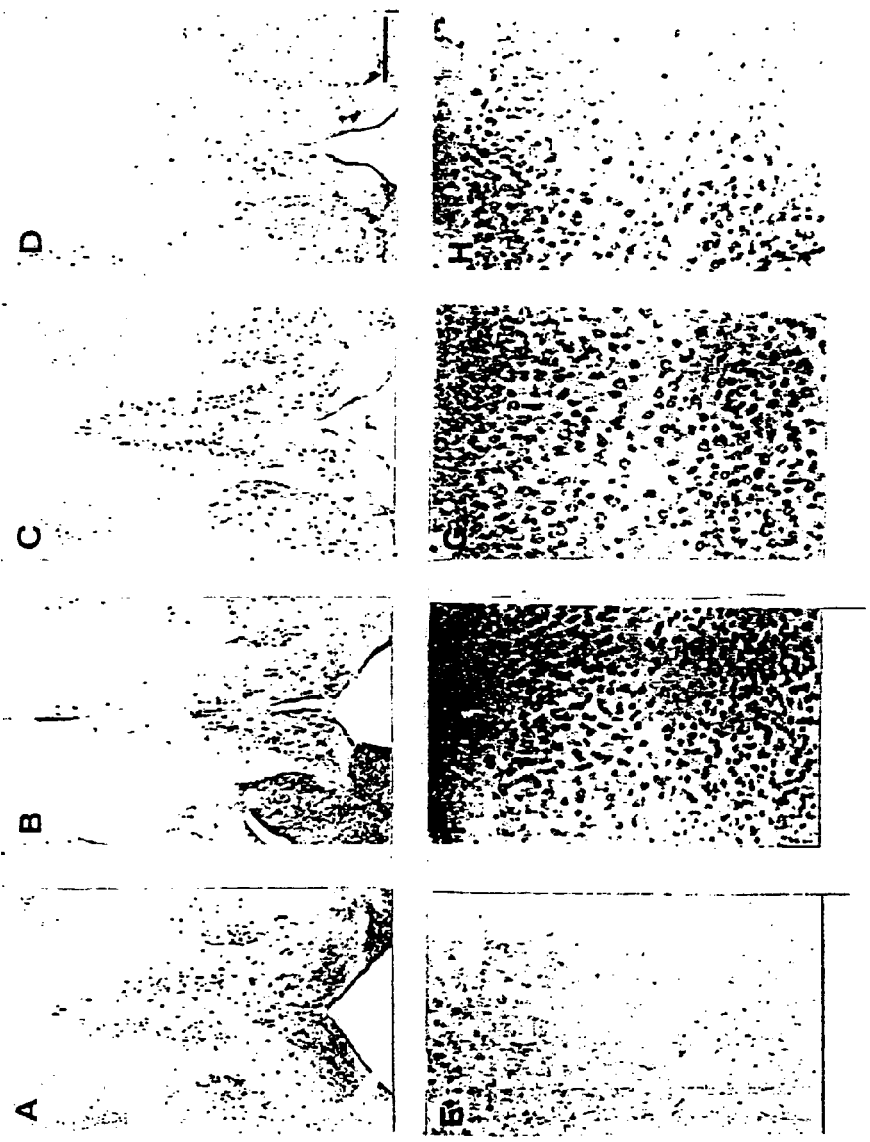
FIG. 32 Immunohistochemistry Data reveals that the number of basal forebrain ChAT-positive neurons in 2-months old AD11 mice is decreased (B) with respect to transgenic control (A). The intraventricular administration of peptide 18 restores the number of ChAT-positive neurons (C) while the injection of a NT-3 related peptide does not allow the rescue of the number of cholinergic neurons (D). Hyperphosphorylated tau is localized in the soma of neurons in the entorhinal cortex of anti-NGF mice (F) with respect to control mice (E). The treatment with peptide 18 decreases the expression in the soma (G) while the administration of the non related peptide is not affecting tau expression (H). Scale bar 320 mm.
Figure 33:
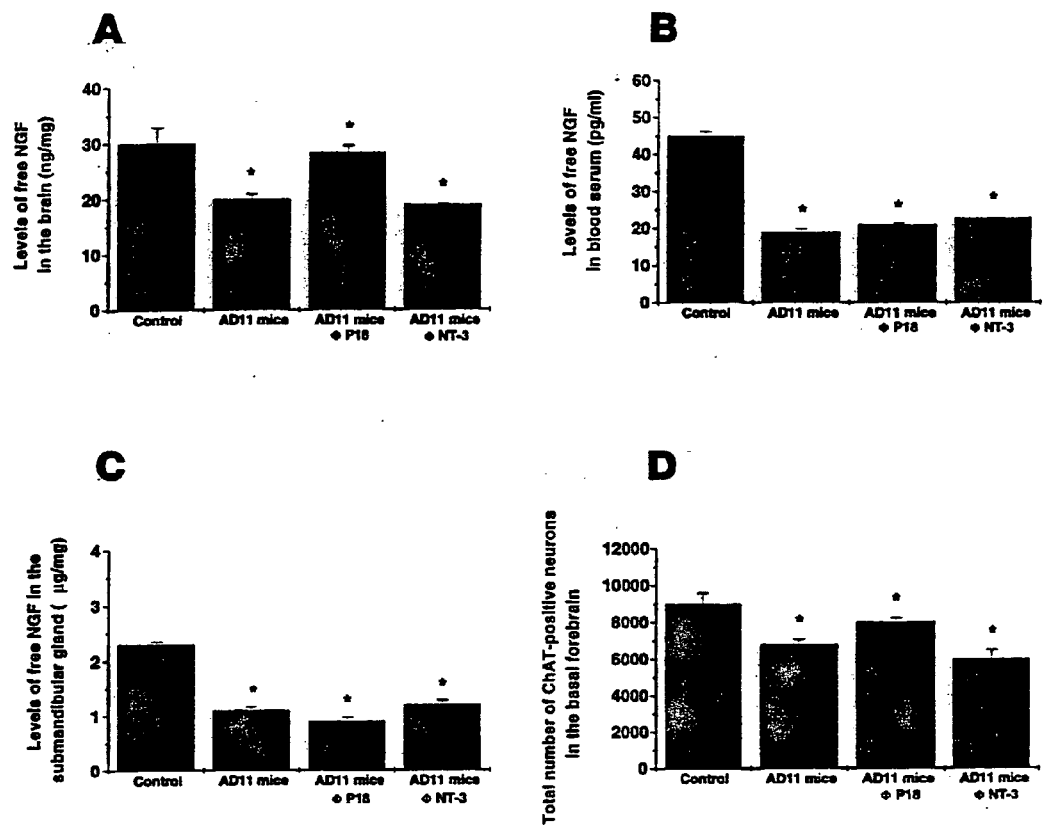
FIG. 33 Analysis of free NGF levels in the brain (A), blood serum (B) and submandibular gland (C) from control mice, AD11 mice, AD11 mice treated with phage carrying the peptide 18 or the NT-3 related peptide. (D) Total number of ChAT-positive neurons in control mice, AD11 mice, AD11 mice treated with phage carrying the peptide 18 or the NT-3 related peptide.

Peptide 18 intraventricular injections. The analysis number of ChAT positive neurons in the basal forebrain of anti-NGF mice revealed a decrease around 40% with respect to transgenic control mice (FIGS. 32A,B, FIG. 33D). The intraventricular administration of the phage carrying the peptide 18 restored the number of ChAT positive neurons in the basal forebrain of the anti-NGF mice to normal values (FIG. 32C, FIG. 33D) while the injection of the peptide binder of anti-NT-3 did not restore the normal values of ChAT-positive neurons (FIG. 32D, FIG. 33D).

In anti-NGF mice hyperphosphorylated tau is localized in the soma of neurons of the entorhinal cortex (FIG. 32F) with respect to control (FIG. 32E). The rescue of the cholinergic phenotype is not paralleled by the disappearance of AT8 labeling in the somatic compartment of neurons of the entorhinal cortex both in animals treated with peptide 18 (FIG. 32G) and in those treated with the non related peptide for anti-NT-3 (FIG. 32H). Concerning the values of free NGF, they increase only at the level basal forebrain, corresponding to the brain area next to the injection site. (FIG. 33A). In blood serum (FIG. 33B) and submandibular gland (FIG. 33C) NGF levels were equal to animals treated with the non related peptide binder of anti-NT-3.

Figure 34:
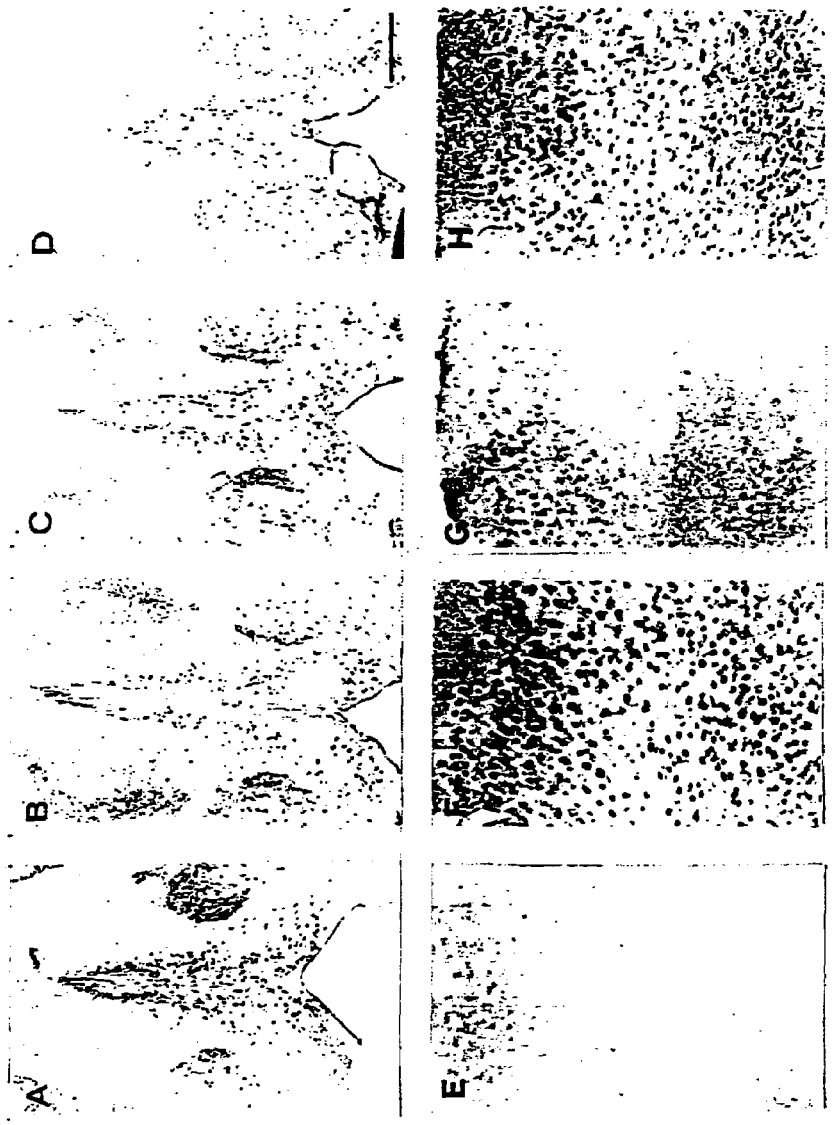
FIG. 34 Immunohistochemistry reveals that the number of basal forebrain ChAT-positive neurons in 2-months old AD11 mice is decreased (Fig. B) with respect to transgenic control (A). The intraperitoneal administration of LT4 restores the number of ChAT-positive neurons (C) while the injection the vehicle does not allow the rescue of the number of cholinergic neurons (D). Hyperphosphorylated tau is localized in the soma of neurons in the entorhinal cortex of anti-NGF mice (F) with respect to control mice (E). The treatment with LT4 decreases the expression in the soma (G) while the administration of vehicle is not affecting tau expression (H). Scale bar 320 mm.
Figure 35:
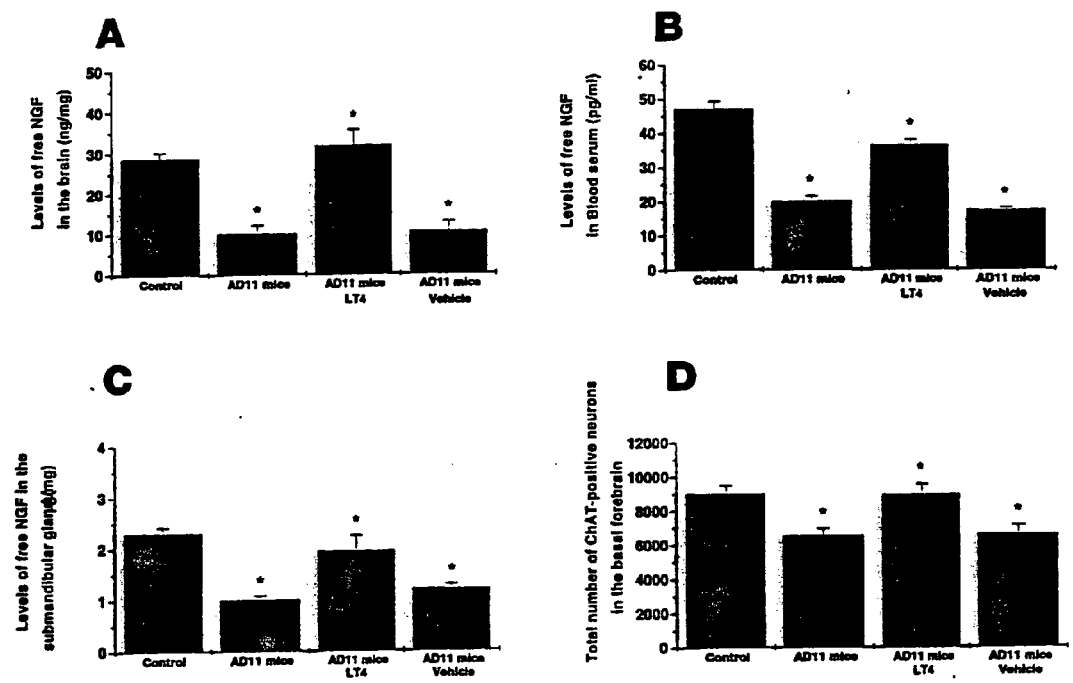
FIG. 35 Analysis of free NGF levels in the brain (A), blood serum (B) and submandibular gland (C) from control mice, AD111 mice, AD11 mice treated with LT4 or vehicle. (D) Total number of ChAT-positive neurons in control mice, AD11 mice, AD11 mice treated with LT4 or vehicle.

LT4 treatment. The intraperitoneal injection of LT4 produces an increase of the number of ChAT-positive neurons in the basal forebrain of anti-NGF anti-NGF mice (FIG. 34C, FIG. 35D). The number of cells was equal to that observed in transgenic control animals (FIG. 34A, FIG. 35D) and was 40% higher than that observed in not-treated anti-NGF mice (FIG. 34B, FIG. 35D) or in animals treated with vehicle (FIG. 34D, FIG. 35D).

In anti-NGF mice hyperphosphorylated tau is localized in the soma of neurons of the entorhinal cortex (FIGS. 34E,F). The rescue of the cholinergic phenotype was paralleled by the disappearance of AT8 labeling in the somatic compartment of neurons of the entorhinal cortex (FIG. 34G), while the administration of the vehicle did not affect the expression of tau (FIG. 34H).

The analysis of NGF levels in brain, blood serum and submandibular gland revealed that, in anti-NGF mice treated with LT4, the amount of free NGF was higher than that detected in animals treated with vehicle (FIG. 35A, B, C). The values obtained reached almost the levels detectable in transgenic control animals.

EXAMPLE 7

Electrophysiological Data

Dysfunction of basal forebrain cholinergic neurons affects experience-dependent plasticity (Gu & Singer, 1993) and is involved in major human cognitive impairments (Dunnett et al., 1991). Recent in vivo experiments indicate that NGF modulates cortical plasticity in the sensory cortex both during postnatal development (Domenici et al., 1991; Domenici et al., 1993; Domenici et al., 1994) and in adulthood (Gu et al., 1994). Experiments on rat visual cortex slices showed that NGF controls the expression of long term potentiation (LTP), an action mediated by the cholinergic system (Pesavento et al., 2000).

The authors decided (i) to analyze, at the neurophysiological level, the effects of chronic NGF deprivation on BFCNs and cortical experience-dependent plasticity; and (ii) to attempt the rescue of the cholinergic deficit and hence the functional alterations in the cerebral cortex, by the administration of NGF and/or cholinergic agonists.

Materials and Methods

Visual cortex slices preparation and electrophysiological recordings. Postsynaptic field potentials were recorded in rat in vitro slices containing visual cortex, following previously described methods (Kirkwood and Bear, 1994). Anti-NGF and transgenic control mice were deeply anesthetized with urethane and then decapitated. The brain was rapidly removed and visual cortex slices (400 μm) prepared and superfused in a submerged recording chamber at 33° C. with gassed artificial cerebrospinal fluid (aCSF) at a rate of 4 ml/min.

Extracellular field potentials in the inferior half of cortical layers 2/3 were recorded with an electrode filled with a 2M NaCl solution and evoked by stimulation of the white matter containing geniculo-cortical fibers, using a bipolar concentric stimulating electrode. The amplitude of the maximum negative field potential in layer 2/3 was used as a measure of the evoked population excitatory current. LTP was induced by 3 trains of high frequency stimulation (HFS, 100 Hz, 1 s). Experiments were performed at different postnatal ages 6 months, when the functional maturation of the visual cortex is completed. Acetylcholine dependence of LTP was investigated by locally delivering through the recording pipette. The amplitude of the maximum negative field potential in layer 2/3 was used as a measure of the evoked population excitatory current. The magnitude of both LTP was measured starting 30 min after the end of the corresponding conditioning protocol. Data for each experimental group were pooled and expressed as percentage change from control baseline, PCCB±S.E.M. Statistical comparison was done by applying a t-test and Mann-Whitney Rank Sum Test between baseline and LTP mean values.

Results

Figure 36:
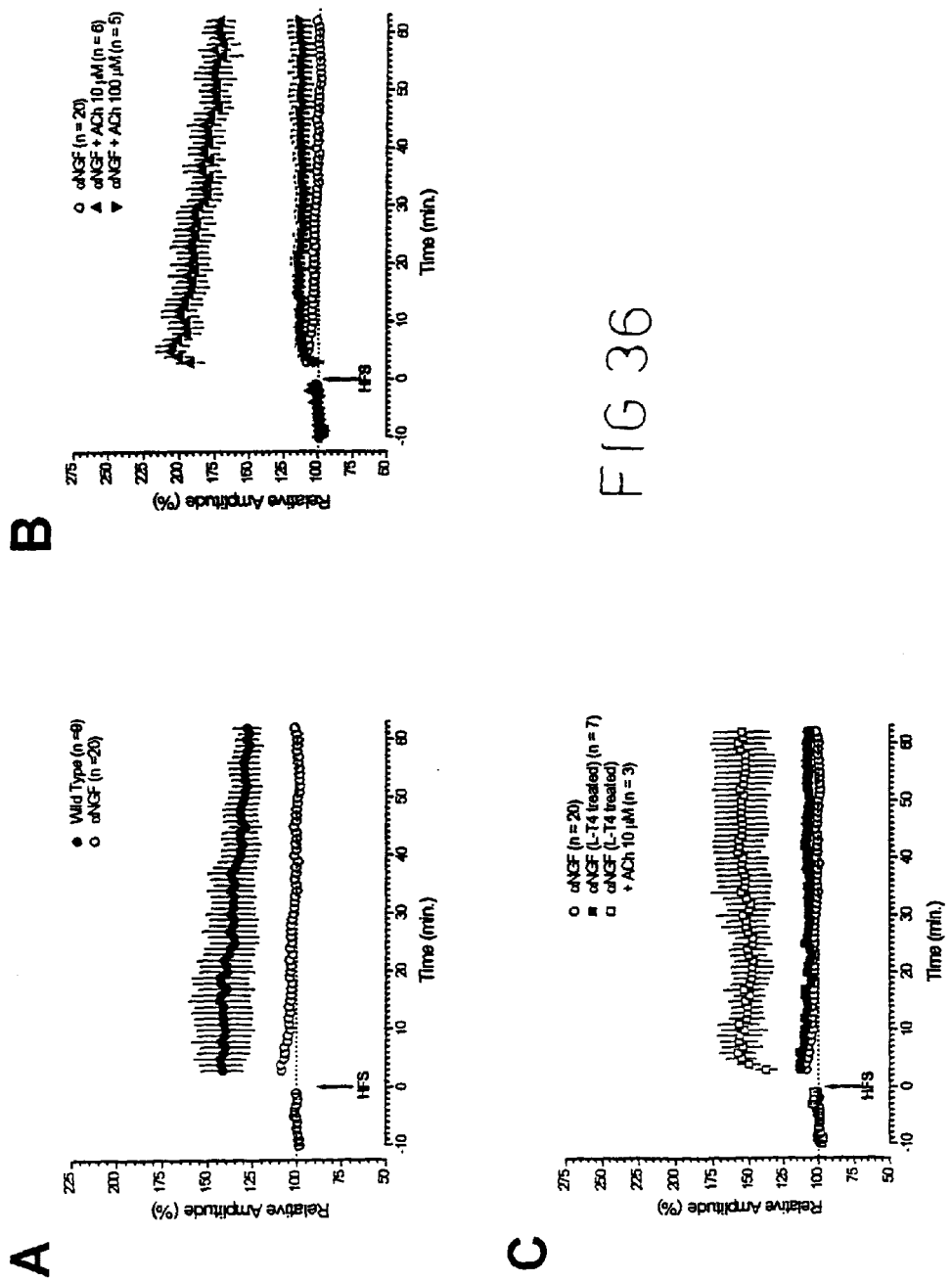
FIG. 36 A) Transgenic mice producing anti-NGF antibody (αNGF) show impairment of synaptic transmission Long-Term Potentiation (LTP) in visual cortex, induced by High Frequency stimulation (HFS) of the white matter, as compared with wild type mice. B) Exogenous supply of acetylcholine (ACh), to αNGF mice, is able to rescue LTP, in a concentration dependent manner. C) Four weeks of systemic administration of thyroid hormone (L-T4) to αNGF mice is not able to rescue plasticity by itself, but increase sensitivity to ACh, that at 10 µM concentration is already effective in the rescue of LTP as compared with L-T4 untreated αNGF mice.

In adult anti-NGF mice, chronic deprivation of NGF determined a decrease in cortical experience-dependent plasticity. In anti-NGF mice, slices containing the visual cortex do not display a particular form of synaptic plasticity, Long Term Potentiation (LTP) (FIG. 36A).

The abnormality in LTP was rescued by adding in the recording chamber acetylcholine (100 □□M). At lower concentration (10 □M), acetylcholine was ineffective (FIG. 36B).

L-thyroxine is an hormone that increases the levels of endogenous NGF in mouse brain (Giordano et al., 1992). The treatment of anti-NGF mice with L-thyroxine (12 □g/animal/day) for 4 weeks allowed only a mild rescue of synaptic plasticity (FIG. 36C). However, in these animals a lower dose of acetylcholine (10 □m), that was per se ineffective, is sufficient to obtain normal levels of LTP (FIG. 36C).

It can be concluded that:

1) Chronic NGF deprivation determines a decreased synaptic plasticity in the visual cortex of anti-NGF mice.

2) This deficit can be rescued by acetylcholine, that can be linked to the decreased cholinergic innervation of the cortex (Ruberti et al., 2000).

3) Treating mice with L-thyroxine restores NGF levels in the cortex. Although NGF is not sufficient to restore synaptic plasticity in the cortex, it facilitates acetylcholine actions, allowing decreasing acetylcholine amount to be delivered.

BIBLIOGRAPHY

Allen, N D, et al. (1987) In Mammalian development: A practical approach, M. Monk, ed. (Washington D.C.: IRL Press) pp 217–234.
Baron P., et al. (1994) Muscle and Nerve 17: 276–284.
Berardi N, et al. (1993). Proc. R. Soc. Lond. B 251:125–131.
Boissiere F, et al. (1997). Exp Neurol 145:245–252.
Borchelt D R, et al. (1997). Neuron 19:939–945.
Brion J P, Tremp G, Octave J N (1999). Am J Pathol 154:255–270.
Cattaneo A, Rapposelli B, and Calissano P (1988) J Neurochem 50:1003–1010.
Changeux J P, Duclert A, Sekine S (1992). NY Acad Sci 657:361–378.
Chomcynzski, P, and Sacchi, N (1987). Anal. Biochem. 162:156–159.
Citron M, et al. (1997). Nat Med 3:67–72.
Connor B, Dragunow M (1998) Brain Res Rev 27:1–39.
Crowley, C, et al. (1994). Cell 76:1001–1011
Davies A M (1992). In Sensory Neurons: Diversity, Development and Plasticity, S. Scott, ed. (Oxford. Oxford University Press), pp 194–214.
Domenici L, et al. (1991) Proc. Natl. Acad. Sci. USA 88:8811–8815.
Domenici L, et al (1994) NeuroReport 5:2041–2044.
Eddy, N B and Leimbach, D (1953) J, Pharmacol. Exp. Ther. 107:385–396.
Eide F, Lowenstain D H and Reichardt L F (1993) Exp. Neurol. 121:200–214.
Fukuchi K, et al. (1998) Am J Pathol 153:1687–1693.
Gage, F H, et al. (1990). Prog Brain Res. 86:205–217
Games S, et al. (1995). Nature 373:523–527.
Gibson S J, et al. (1984). J. Neurosci. 4:3101–3111.
Giordano T, et al. (1992) Brain Res. Mol. Brain Res. 16:239–245.
Glenner G C, Wong C W (1984), Biophys Biochem Res Commun 120:885–890.
Goedert M (1993). Trends Neurosci 16:460–465.
Gotz J, et al. (1995). EMBO J. 14:1304–1313.
Greenberg S G, Davies P (1990) Proc Natl Acad Sci USA 87:5827–5831.
Grundke-Iqbal I, et al. (1986). Proc Natl Acad Sci USA 83:4913–4917.
Gu Q, Singer W. (1993) Eur. J. Neurosci. 5:475–485.
Gu Q, Liu Y, Cynader M S. (1994). Proc. Natl. Acad. Sci. USA 91, 8408–8412.
Holcomb L, et al. (1998). Nat Med. 4:97–100
Hsiao K, et al. (1996). Science 274:99–102.
Irizarry M C, et al. (1997b). J Neurosci 17:7053–7059.
Jin L W, et al. (1998). Am J Pathol 153:1679–1686.
Kalaria R N (1993). Brain Pathol 3:333–347.
Kirkwood A. and Bear, M (1994). J. Neurosci. 14:1634–1645.
Levi-Montalcini R and Brooker (1960). Proc. Natl. Acad Sci USA 46:384–391.
Luesse H G, et al., (1998) Exp. Brain Res. 119, 1–8.
Luxenberg J S, et al. (1987). Neurology 37:1135–1140.
Mandelkow E M, Mandlekow E (1993). Trends Biochem Sci 18:480–483.
Mizutani T, et al. (1990) Acta Neuropathol (Berl) 80:575–580.
Molnar, M et al. (1998). Eur. J. Neurosci. 10:3127–3140.
Pesavento E, et al. (2000) Neuron 25, 165–175, 2000.
Piccioli, P et al. (1995). Neuron 15:373–384.
Raynaud, J. (1964) In: Salivary Glands and Their Secretion. Srrebny L M, Meyer J. (eds.), Pergamon Press, London, p. 47.
Ruberti F, Bradbury A and Cattaneo A (1993). Cell Mol Neurobiol 13:559–568.
Ruberti F, et al. (2000) J. Neurosci 20:2589–2601.
Schnell L. et al. (1994). Nature 367:170–173.
Selkoe D J (1994). Curr Opin Neurobiol 4:708–716.
Snider W D and Johnson E M Jr (1989). Ann. Neurol. 26:489–506.
Sturchler-Pierrat C, et al. (1997). Proc Natl Acad Sci USA 94:13287–13292.
Wolozin B L, et al. (1986). Science 232:648–650.
Wong T P, et al. (1999). J Neurosci 19:2706–2716.

All publications, patents, and patent applications cited in this specification are herein incorporated by reference as if each individual publication or patent application were specifically and individually indicated to be incorporated by reference.

The invention claimed is:

1. A transgenic mouse whose genome comprises transgenes comprising sequences that encode a variable heavy chain and a variable light chain of an NGF-specific antibody or fragment thereof, wherein the expressed transgene products combine to form an antibody or fragment thereof that is specific for NGF and prevents binding of NGF to its receptors, said transgenes being detectably expressed in the mouse by 90 days postnatal, and said mouse having, or being predisposed to the development of (a) abnormally processed amyloid precursor protein, (b) amyloid precursor protein and/or β-amyloid protein plaques in the CNS, (c) hyperphosphorylation of tau protein, (d) neurofibrillary tangles in the brain, (e) cholinergic deficit, (f) neuronal loss in the cortex of the brain, and (g) cognitive deficit.

2. A transgenic mouse according to claim 1, wherein the neurodegenerative pathology is present in the mouse by 15 to 18 months of age.

3. A transgenic mouse according to claim 1, wherein the anti-NGF antibody is expressed in adulthood.

4. A transgenic mouse according to claim 3, wherein the anti-NGF antibody in the serum of the adult animal is at a level of between 50 ng/ml and 500 ng/ml.

5. The transgenic mouse of claim 1, that:
    (a) is heterozygous for a transgene encoding a variable heavy chain and heterozygous for a transgene encoding a variable light chain of an anti-NGF antibody; and,
    (b) produces a fully constituted anti-NGF antibody comprising said variable heavy and light chains that is present in the serum of the mouse at a level of at least 50 ng/ml by postnatal day 90.

6. A transgenic mouse according to claim 5, wherein the variable heavy chain and the variable light chain correspond to the variable heavy chain and variable light chain of anti-NGF monoclonal antibody αD11.

7. A transgenic mouse according to claim 6, wherein the variable heavy chain is linked to a human γ1 constant region and the variable light chain is linked to a human k constant region, thereby producing a chimeric anti-NGF antibody.

8. A transgenic mouse according to claim 7, wherein the chimeric anti-NGF antibody is a humanised chimeric antibody.

9. A transgenic mouse according to claim 1 belonging to the *Mus musculus* B6SJL strain.

10. Isolated brain tissue from the mouse of claim 1.

11. Isolated skeletal muscle tissue from the mouse of claim 1.

12. A transgenic mouse whose genome comprises transgenes comprising sequences that encode a variable heavy chain and a variable light chain of an NGF-specific antibody or fragment thereof, wherein the expressed transgene products combine to form an antibody or fragment thereof that is specific for NGF and prevents binding of NGF to its receptors, said transgenes being detectably expressed in the mouse by 90 days postnatal, and said mouse having, or being predisposed to the development of at least two of the following characteristics: (a) abnormally processed amyloid precursor protein, (b) amyloid precursor protein and/or β-amyloid protein plaques in the CNS, (c) hyperphosphorylation of tau protein, (d) neurofibrillary tangles in the brain, (e) cholinergic deficit, (f) neuronal loss in the cortex of the brain, and (g) cognitive deficit.

* * * * *